United States Patent
Perkins et al.

(10) Patent No.: US 11,779,693 B2
(45) Date of Patent: Oct. 10, 2023

(54) NEGATIVE-PRESSURE WOUND THERAPY DRESSING WITH ZONE OF AMBIENT PRESSURE

(71) Applicant: KCI Licensing, Inc., San Antonio, TX (US)

(72) Inventors: Luke Perkins, San Antonio, TX (US); Christopher J. Carroll, San Antonio, TX (US); Shervin Jahanian, San Antonio, TX (US); Jonathan G. Rehbein, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 17/795,784

(22) PCT Filed: Mar. 17, 2021

(86) PCT No.: PCT/IB2021/052218
§ 371 (c)(1),
(2) Date: Jul. 27, 2022

(87) PCT Pub. No.: WO2021/191744
PCT Pub. Date: Sep. 30, 2021

(65) Prior Publication Data
US 2023/0090100 A1 Mar. 23, 2023

Related U.S. Application Data

(60) Provisional application No. 62/993,929, filed on Mar. 24, 2020.

(51) Int. Cl.
*A61M 1/00* (2006.01)
*A61F 13/14* (2006.01)

(52) U.S. Cl.
CPC ........... *A61M 1/915* (2021.05); *A61F 13/145* (2013.01); *A61M 1/917* (2021.05); *A61M 2210/1007* (2013.01)

(58) Field of Classification Search
CPC ................. A61M 1/915; A61M 1/917; A61M 2210/1007; A61M 1/90; A61M 27/00; A61F 13/145
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 B2 | 3/1986 | |
| AU | 745271 B2 | 3/2002 | |

(Continued)

OTHER PUBLICATIONS

International Search Report and Written Opinion for Corresponding Application No. PCT/IB2021/052218, dated Jun. 16, 2021.

(Continued)

*Primary Examiner* — Sarah Al Hashimi
*Assistant Examiner* — Nhu Q. Tran

(57) ABSTRACT

Disclosed embodiments may relate to dressings configured to provide negative-pressure wound therapy to a tissue site, while simultaneously shielding a portion of the tissue site from the negative pressure. For example, dressing assembly embodiments may comprise an outer dressing configured for applying negative-pressure wound therapy to a tissue site, and an underlying isolation patch configured for use under the outer dressing. The isolation patch may be configured to seal the portion of the tissue site so that it does not (Continued)

experience the negative pressure. Additionally disclosed are other apparatus, dressings, systems, and methods.

27 Claims, 12 Drawing Sheets

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Mair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0299257 A1* | 12/2009 | Long .................... A61M 1/71 602/53 |
| 2014/0163491 A1 | 6/2014 | Schuessler et al. |
| 2015/0032035 A1 | 1/2015 | Banwell et al. |
| 2015/0080788 A1 | 3/2015 | Blott et al. |
| 2019/0125590 A1 | 5/2019 | Rehbein et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |

(56) References Cited

FOREIGN PATENT DOCUMENTS

| | | |
|---|---|---|
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2018212849 A1 | 11/2018 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, Nos. May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 pages English translation thereof.
Davydov, Yu. A., et al; "Vacuum Therapy in the Treatment of Purulent Lactation Mastitis"; Vestnik Khirurgi, May 14, 1986, pp. 66-70, and 9 pages English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

NEGATIVE-PRESSURE WOUND THERAPY DRESSING WITH ZONE OF AMBIENT PRESSURE

CROSS-REFERENCE TO RELATED APPLICATIONS

This application claims the benefit of priority to U.S. Provisional Application No. 62/993,929, filed on Mar. 24, 2020, which is incorporated herein by reference in its entirety.

TECHNICAL FIELD

This disclosure relates generally to tissue treatment systems and more particularly, but without limitation, to dressings, systems, and methods relating to negative-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for managing tissue sites in a negative-pressure therapy environment are set forth in the appended claims. The following description provides non-limiting, illustrative example embodiments to enable a person skilled in the art to make and use the claimed subject matter.

Disclosed embodiments may relate to dressings configured to provide negative-pressure wound therapy to a tissue site, while simultaneously shielding a portion of the tissue site from the negative pressure. For example, dressing embodiments may comprise an outer negative-pressure dressing configured for applying negative-pressure therapy to a tissue site, and an underlying isolation patch, such as a zone of ambient pressure (ZAP) patch, configured for use under the negative-pressure dressing. The isolation patch may be configured to seal the portion of the tissue site so that it does not experience negative pressure, despite being located under the negative-pressure dressing. In some embodiments, the isolation patch may be vented (e.g. via tubing) to ambient atmosphere outside the negative-pressure dressing, for example to maintain ambient pressure. In other embodiments, the isolation patch may not be vented, but may seal ambient pressure over the portion of the tissue site which is not to experience negative pressure. In some embodiments, the isolation patch may be configured to resist appositional and/or decompressive forces, for example arising due to negative-pressure wound therapy.

In some example embodiments, a dressing assembly may comprise: a negative-pressure dressing configured for application of negative pressure to a tissue site; and an isolation patch configured for use under the negative-pressure dressing and configured to isolate a portion of the tissue site from the negative pressure (for example, by maintaining ambient environment pressure to form a zone of ambient pressure). In some embodiments, the isolation patch may comprise a force-dissipating pad, which may for example comprise a manifold or a gel layer, configured to resist appositional and/or decompressive forces. In some embodiments, the isolation patch may be configured to prevent fluid communication between the isolation patch and the negative-pressure dressing. Some embodiments of the isolation patch may comprise: a first manifold; a first cover configured to be disposed over the first manifold and to substantially prevent fluid flow therethrough; a first attachment device configured to attach the first cover to the isolated portion of the tissue site and to form a seal preventing fluid communication between the isolated portion of the tissue site under the isolation patch and the remainder of the tissue site (e.g. a negative-pressure zone) under the negative-pressure dressing; and a vent configured to fluidly couple the first manifold to an ambient environment. Other embodiments of the isolation patch may comprise a patch manifold, a patch cover configured to be disposed over the patch manifold, and a vent to ambient environment. In some embodiments, the isolation patch may further comprise a patch attachment device configured to seal the patch cover to the portion of the tissue site. Some embodiments of the negative-pressure dressing may comprise: a second manifold; a second cover configured to be disposed over the second manifold and to substantially prevent fluid flow therethrough; and a second attachment device configured to attach the negative-pressure dressing to the tissue site and to form a seal preventing fluid communication between the tissue site and the ambient environment. Other embodiments of the negative-pressure dressing may comprise a dressing attachment device having a dressing treatment aperture; a dressing manifold configured to be at least partially exposed to the tissue site through the dressing treatment aperture; and a dressing cover configured to be disposed over the dressing manifold and coupled to the dressing attachment device around the dressing manifold. In some embodiments, the vent may further comprise a ventilation conduit with a proximal end fluidly coupled to the patch manifold and a distal end configured to be located external to the negative-pressure dressing and fluidly coupled to the ambient environment (for example, passing under the negative-pressure dressing in proximity to the dressing attachment device). The vent may be configured to pass through the negative-pressure dressing (e.g. through the dressing cover) in other embodiments. In some embodiments, the isolation patch may comprise a gel layer and a patch cover configured to be disposed over the gel layer to form an outer surface of the isolation patch. In some embodiments, the patch cover may be occlusive with high MVTR. The gel layer may be occlusive, in some embodiments. For example, the gel layer may comprise thermoplastic elastomer (TPE) gel.

In some example embodiments, a system for providing negative-pressure therapy may comprise: a dressing assembly and a negative-pressure source. In some embodiments, the dressing assembly may comprise any of those described above. For example, the dressing assembly may comprise a negative-pressure dressing configured for application of negative pressure to a tissue site; and an isolation patch, configured for use under the negative-pressure dressing and configured to fluidly isolate a portion of the tissue site from the negative pressure. The negative-pressure source may be fluidly coupled to the negative-pressure dressing in some embodiments.

In some example embodiments, a dressing, for use on a tissue site, may be configured to have two zones: a negative-pressure zone and a zone of ambient pressure; and the two zones may be fluidly isolated from each other (e.g. the two zones may have substantially no fluid communication therebetween). In some embodiments, the negative-pressure zone may be formed by a negative-pressure dressing configured for negative-pressure therapy at the tissue site; and the zone of ambient pressure may be formed by an isolation patch configured to underlie the negative-pressure dressing and to maintain ambient environment pressure at a portion of the tissue site. In some embodiments, the negative-pressure zone may be configured to allow application of negative pressure to the tissue site, and the zone of ambient pressure may be configured to prevent application of the negative pressure to the portion of the tissue site. In some embodiments, the negative-pressure zone may be configured to surround the zone of ambient pressure over the tissue site. In some embodiments, the zone of ambient pressure may be configured to lie within the negative-pressure zone, to maintain ambient pressure while surrounded by the negative-pressure zone, and/or to resist or protect against appositional and/or decompressive forces.

In some example embodiments, a method, for using a dressing assembly (or two-part dressing) on a tissue site, may further comprise: applying an isolation patch to a portion of the tissue site; and applying a negative-pressure dressing to the tissue site, over the isolation patch. In some embodiments, applying the isolation patch may comprise sealing the isolation patch over the portion of the tissue site to form a first sealed space with ambient pressure; and applying the negative-pressure dressing may comprise sealing the negative-pressure dressing over the isolation patch and the tissue site, to form a second sealed space configured for negative pressure wound therapy. Some method embodiments may further comprise fluidly coupling the isolation patch to an ambient environment. Some embodiments may further comprise fluidly coupling the negative-pressure dressing to a negative-pressure source and applying negative pressure through the negative-pressure dressing to the tissue site, except for the portion of the tissue site isolated by the isolation patch. In some embodiments, the dressing or dressing assembly may be similar to those discussed above.

In some example embodiments, a method for providing negative pressure wound therapy to a tissue site may comprise: fluidly isolating a portion of the tissue site (e.g. from negative pressure); sealing the tissue site for negative-pressure wound therapy; and applying negative pressure to the tissue site, except at the isolated portion of the tissue site. In some method embodiments, fluidly isolating a portion of the tissue site may comprise applying an isolation patch; and sealing the tissue site may comprise applying a negative-pressure dressing over the isolation patch and the tissue site. In some embodiments, applying an isolation patch may comprise sealing the isolation patch over a portion of the tissue site to form a first sealed space with ambient pressure; and applying a negative-pressure dressing may comprise sealing the negative-pressure dressing over the isolation patch and the tissue site, to form a second sealed space configured for negative pressure. In some embodiments, fluidly isolating a portion of the tissue site from negative pressure may further comprise preventing substantially any fluid communication between the first sealed space and the second sealed space. In some embodiments, the isolation patch may be un-vented, and fluidly isolating the portion of the tissue site may comprise preventing substantially any fluid communication into and/or out of the isolation patch. In some embodiments, fluidly isolating a portion of the issue site from negative pressure may further comprise fluidly coupling the isolation patch to the ambient environment, for example fluidly coupling the first sealed space to the ambient environment.

Objectives, advantages, and a preferred mode of making and using the claimed subject matter may be understood best by reference to the accompanying drawings in conjunction with the following detailed description of illustrative example embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and non-limiting.

Figure 1:
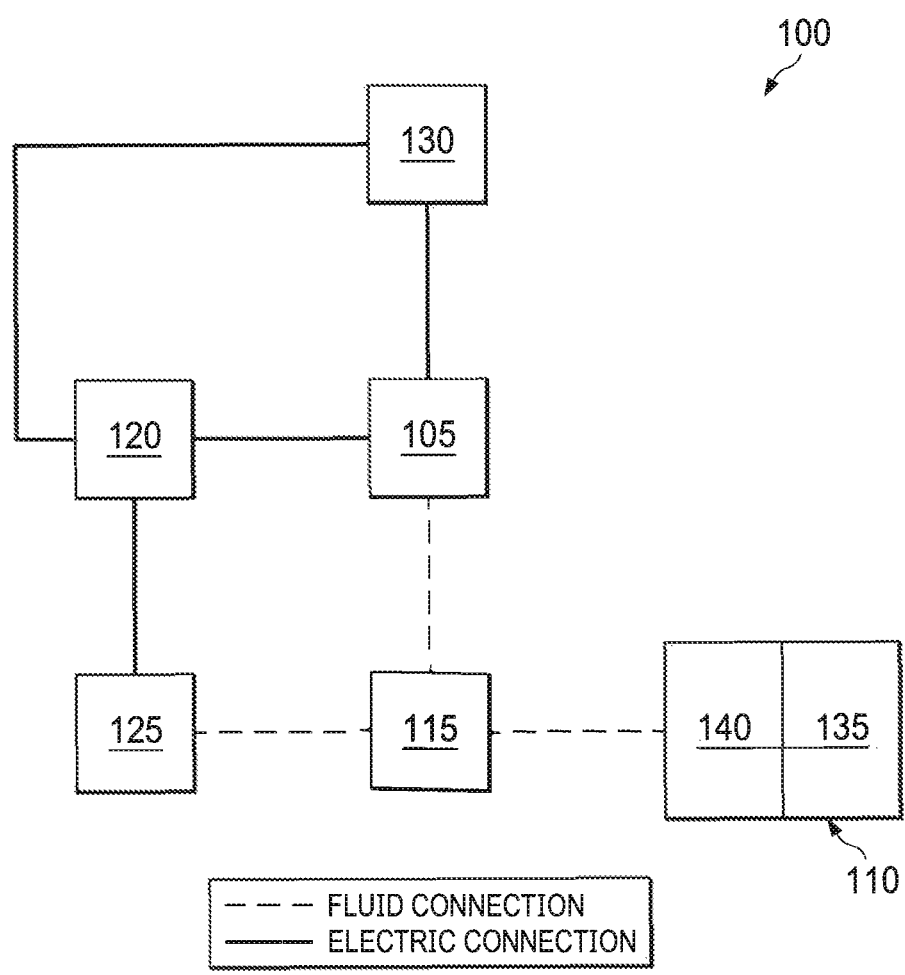
FIG. 1 is a block diagram of an example embodiment of a therapy system that can provide negative-pressure therapy in accordance with this specification.

FIG. 1 is a block diagram of an example embodiment of a therapy system 100 that can provide negative-pressure therapy to a tissue site in accordance with this specification. The term "tissue site" in this context may refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, and incisions, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of reduced or negative pressure, such as a negative-pressure source 105, a dressing 110, a fluid container, such as a container 115, and a regulator or controller, such as a controller 120, for example. Additionally, the therapy system 100 may include sensors to measure operating parameters and provide feedback signals to the controller 120 indicative of the operating parameters. As illustrated in FIG. 1, for example, the therapy system 100 may include one or more sensors coupled to the controller 120, such as a first sensor 125 and a second sensor 130. As illustrated in the example of FIG. 1, the dressing 110 may include a tissue interface 135, a cover 140, or both in some embodiments. The dressing 110 may also be referred to as a dressing assembly in some examples, which may include additional or different features as described herein.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 120 and other components into a therapy unit.

In general, components of the therapy system 100 may be coupled directly or indirectly. For example, the negative-pressure source 105 may be directly coupled to the container 115, and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 120, and may be fluidly coupled to one or more distribution components to provide a fluid path to a tissue site. In some embodiments, components may also be coupled by virtue of physical proximity, being integral to a single structure, or being formed from the same piece of material.

A distribution component may be detachable, and may be disposable, reusable, or recyclable. The dressing 110 and the container 115 are illustrative of distribution components. A fluid conductor is another illustrative example of a distribution component. A "fluid conductor," in this context, may include a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad available from KCI of San Antonio, Tex.

A negative-pressure supply, such as the negative-pressure source 105, may be a reservoir of air at a reduced pressure, or may be a manual or electrically-powered device, such as a vacuum pump, a suction pump, a wall suction port available at many healthcare facilities, or a micro-pump, for example. "Negative pressure" or "reduced pressure" generally refers to a pressure less than a local ambient pressure, such as the ambient pressure in a local environment external to a sealed therapeutic environment. In many cases, the local ambient pressure may also be the atmospheric pressure at which a tissue site is located. Further, the pressure may be less than a hydrostatic pressure associated with tissue at the tissue site. Unless otherwise indicated, values of pressure stated herein are gauge pressures. References to increases in reduced pressure may refer to a decrease in absolute pressure, while decreases in reduced pressure may refer to an increase in absolute pressure. While the amount and nature of reduced pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 120, may be a microprocessor or computer programmed to operate one or more components of the therapy system 100, such as the negative-pressure source 105. In some embodiments, for example, the controller 120 may be a microcontroller, which may include an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 135, for example. The controller 120 may also be configured to receive one or more input signals, such as a feedback signal, and programmed to modify one or more operating parameters based on the input signals.

Sensors, such as the first sensor 125 and the second sensor 130, may be any apparatus operable to detect or measure a physical phenomenon or property, and generally provide a signal indicative of the phenomenon or property that is detected or measured. For example, the first sensor 125 and the second sensor 130 may be configured to measure one or more operating parameters of the therapy system 100. In some embodiments, the first sensor 125 may be a transducer configured to measure pressure in a pneumatic pathway and convert the measurement to a signal indicative of the pressure measured. In some embodiments, for example, the first sensor 125 may be a piezoresistive strain gauge. The second sensor 130 may optionally measure operating parameters of the negative-pressure source 105, such as the voltage or current, in some embodiments. Signals from the first sensor 125 and the second sensor 130 may be suitable as an input signal to the controller 120, but some signal conditioning may be appropriate in some embodiments. For example, the signal may need to be filtered or amplified before it can be processed by the controller 120. Typically, the signal is an electrical signal, but may be represented in other forms, such as an optical signal.

The tissue interface 135 can be adapted to partially or fully contact a tissue site. The tissue interface 135 may take many forms, and may have many sizes, shapes, or thicknesses depending on a variety of factors, such as the type of treatment being implemented or the nature and size of a tissue site. For example, the size and shape of the tissue interface 135 may be adapted to the contours of deep and irregular shaped tissue sites. Moreover, any or all of the surfaces of the tissue interface 135 may have projections or an uneven, course, or jagged profile that can induce strains and stresses on a tissue site, which can promote granulation at the tissue site.

In some embodiments, the tissue interface 135 may be a manifold or may include a manifold and additional layers, such as a tissue contact layer, depending on the desired treatment. A "manifold" in this context may include any substance or structure providing a plurality of pathways adapted to collect or distribute fluid relative to a tissue. For example, a manifold may be adapted to receive reduced pressure from a source and distribute reduced pressure through multiple apertures to or from a tissue site, which may have the effect of collecting fluid from a tissue site and drawing the fluid toward the source. In some embodiments, the fluid path may be reversed or a secondary fluid path may be provided to facilitate delivering or moving fluid relative to a tissue site.

In some illustrative embodiments, the pathways of a manifold may be interconnected to improve distribution or collection of fluids at a tissue site. In some illustrative embodiments, a manifold may be a porous foam material having interconnected cells or pores. For example, open-cell foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively include projections that form interconnected fluid pathways. For example, a manifold may be molded to provide surface projections that define interconnected fluid pathways.

The average pore size of foam may vary according to needs of a prescribed therapy. For example, in some embodiments, the tissue interface 135 may be foam having pore sizes in a range of 400-600 microns. The tensile strength of the tissue interface 135 may also vary according to needs of a prescribed therapy. For example, the tensile strength of foam may be increased for instillation of topical treatment solutions. In some examples, the tissue interface 135 may be reticulated polyurethane foam such as found in GRANUFOAM™ dressing or V.A.C. VERAFLO™ dressing, both available from KCI of San Antonio, Tex.

The tissue interface 135 may be either hydrophobic or hydrophilic. In an example in which the tissue interface 135 may be hydrophilic, the tissue interface 135 may also wick fluid away from a tissue site, while continuing to distribute negative pressure to the tissue site. The wicking properties of the tissue interface 135 may draw fluid away from a tissue site by capillary flow or other wicking mechanisms. An example of hydrophilic foam is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

The tissue interface 135 may further promote granulation at a tissue site when pressure within the sealed therapeutic environment is reduced. For example, any or all of the surfaces of the tissue interface 135 may have an uneven, coarse, or jagged profile that can induce microstrain and stress at a tissue site if negative pressure is applied through the tissue interface 135.

In some embodiments, the tissue interface 135 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 135 may further serve as a scaffold for new cell-growth, or a scaffold material may be used in conjunction with the tissue interface 135 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 140 may provide a bacterial barrier and protection from physical trauma. The cover 140 may also be constructed from a material that can reduce evaporative losses and provide a fluid seal between two components or two environments, such as between a therapeutic environment and a local external environment. For example, the cover 140 may comprise or consist essentially of an elastomeric film or membrane that can provide a seal adequate to maintain a reduced pressure at a tissue site for a given negative-pressure source. In some example embodiments, the cover 140 may be a polymer drape, such as a polyurethane film, that is permeable to water vapor but impermeable to liquid. The cover 140 may have a high moisture-vapor transmission rate (MVTR) in some applications. For example, the MVTR may be at least 250 g/m^2 per twenty-four hours in some embodiments (based on ASTM E96/E96M for upright cup measurement). Such drapes typically have a thickness in the range of 25-50 microns. For permeable materials, the permeability generally should be low enough that a desired negative pressure may be maintained. In some embodiments, the cover 140 may form an outer surface of the dressing 110.

An attachment device may be used to attach the cover 140 to an attachment surface, such as undamaged epidermis, a gasket, or another cover (e.g. at the tissue site). The attachment device may take many forms. For example, an attachment device may be a medically-acceptable, pressure-sensitive adhesive configured to bond the cover 140 to epidermis around a tissue site. In some embodiments, for example, some or all of the cover 140 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Figure 2:
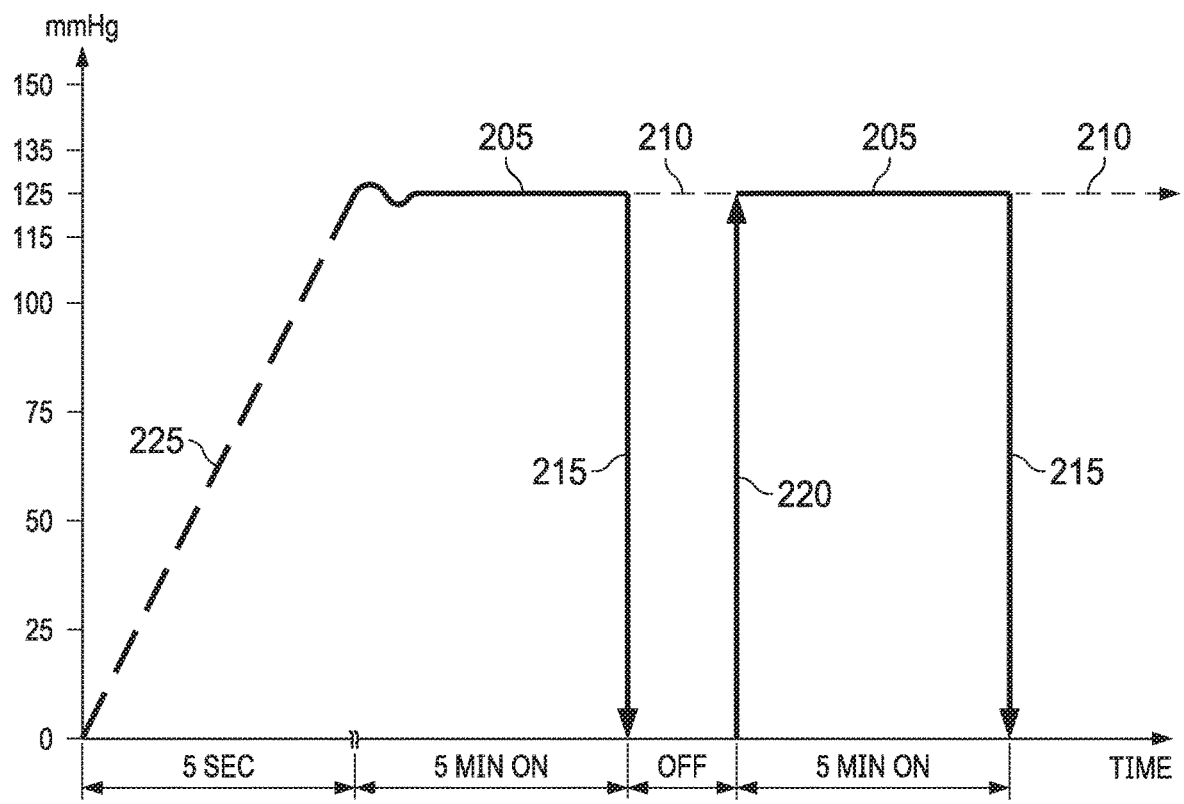
FIG. 2 is a graph illustrating example pressure control modes that may be associated with some example embodiments of the therapy system of FIG. 1.

FIG. 2 is a graph illustrating additional details of an example control mode that may be associated with some embodiments of the controller 120. In some embodiments, the controller 120 may have a continuous pressure mode, in which the negative-pressure source 105 is operated to provide a constant target reduced pressure, as indicated by line 205 and line 210, for the duration of treatment or until manually deactivated. Additionally or alternatively, the controller may have an intermittent pressure mode, as illustrated in the example of FIG. 2. In FIG. 2, the x-axis represents time, and the y-axis represents reduced pressure generated by the negative-pressure source 105 over time. In the example of FIG. 2, the controller 120 can operate the negative-pressure source 105 to cycle between a target pressure and atmospheric pressure. For example, the target pressure may be set at a value of 125 mmHg, as indicated by line 205, for a specified period of time (e.g., 5 min), followed by a specified period of time (e.g., 2 min) of deactivation, as indicated by the gap between the solid lines 215 and 220. The cycle can be repeated by activating the negative-pressure source 105, as indicated by line 220, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time, as indicated by the dashed line 225. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time as indicated by the solid line 220 may be a value substantially equal to the initial rise time as indicated by the dashed line 225.

Figure 3:
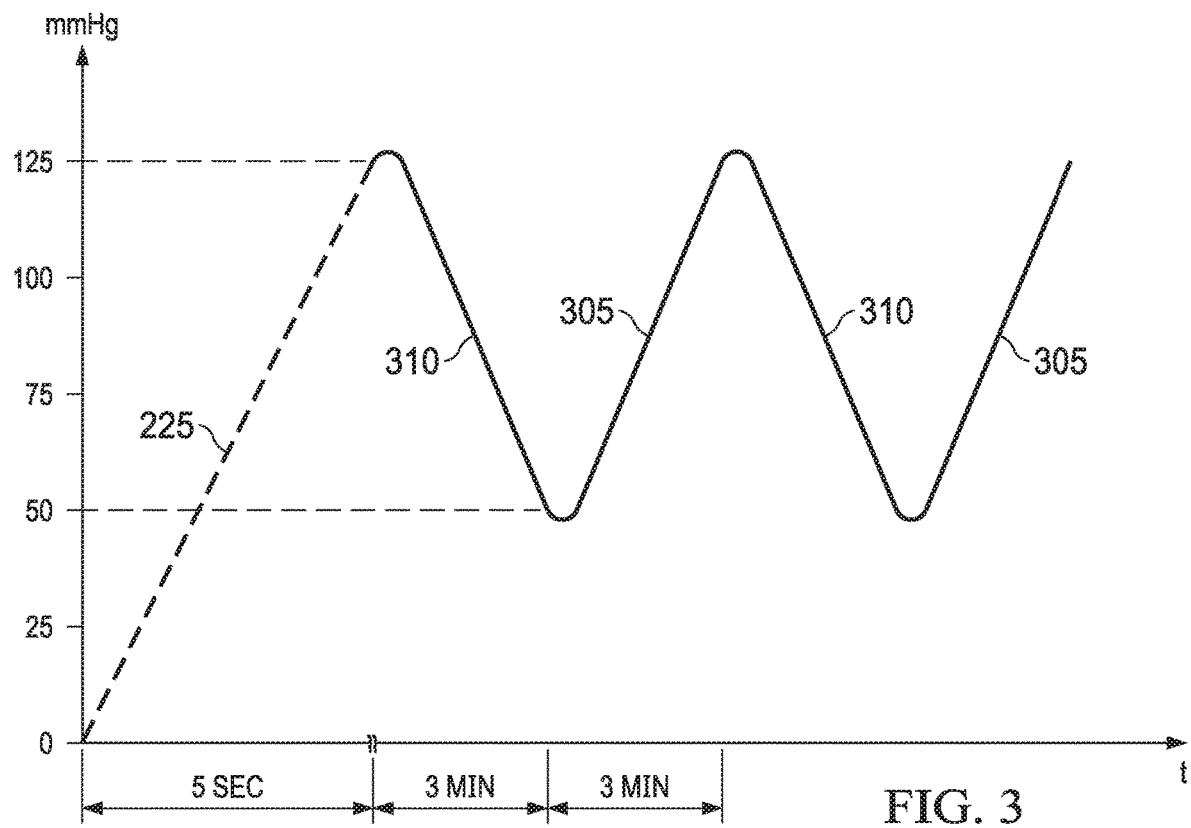
FIG. 3 is a graph illustrating another example pressure control mode suitable for some example embodiments of the therapy system of FIG. 1.

FIG. 3 is a graph illustrating additional details that may be associated with another example pressure control mode in some embodiments of the therapy system 100. In FIG. 3, the x-axis represents time and the y-axis represents negative pressure generated by the negative-pressure source 105. The target pressure in the example of FIG. 3 can vary with time in a dynamic pressure mode. For example, the target pressure may vary in the form of a triangular waveform, varying between a minimum and maximum reduced pressure of 50-125 mmHg with a rise time 305 set at a rate of +25 mmHg/min. and a descent time 310 set at −25 mmHg/min, respectively. In other embodiments of the therapy system 100, the triangular waveform may vary between reduced pressure of 25-125 mmHg with a rise time 305 set at a rate of +30 mmHg/min and a descent time 310 set at −30 mmHg/min.

In some embodiments, the controller 120 may control or determine a variable target pressure in a dynamic pressure mode, and the variable target pressure may vary between a maximum and minimum pressure value that may be set as an input prescribed by an operator as the range of desired reduced pressure. The variable target pressure may also be processed and controlled by the controller 120, which can vary the target pressure according to a predetermined waveform, such as a triangular waveform, a sine waveform, or a saw-tooth waveform. In some embodiments, the waveform may be set by an operator as the predetermined or time-varying reduced pressure desired for therapy.

Figure 4:
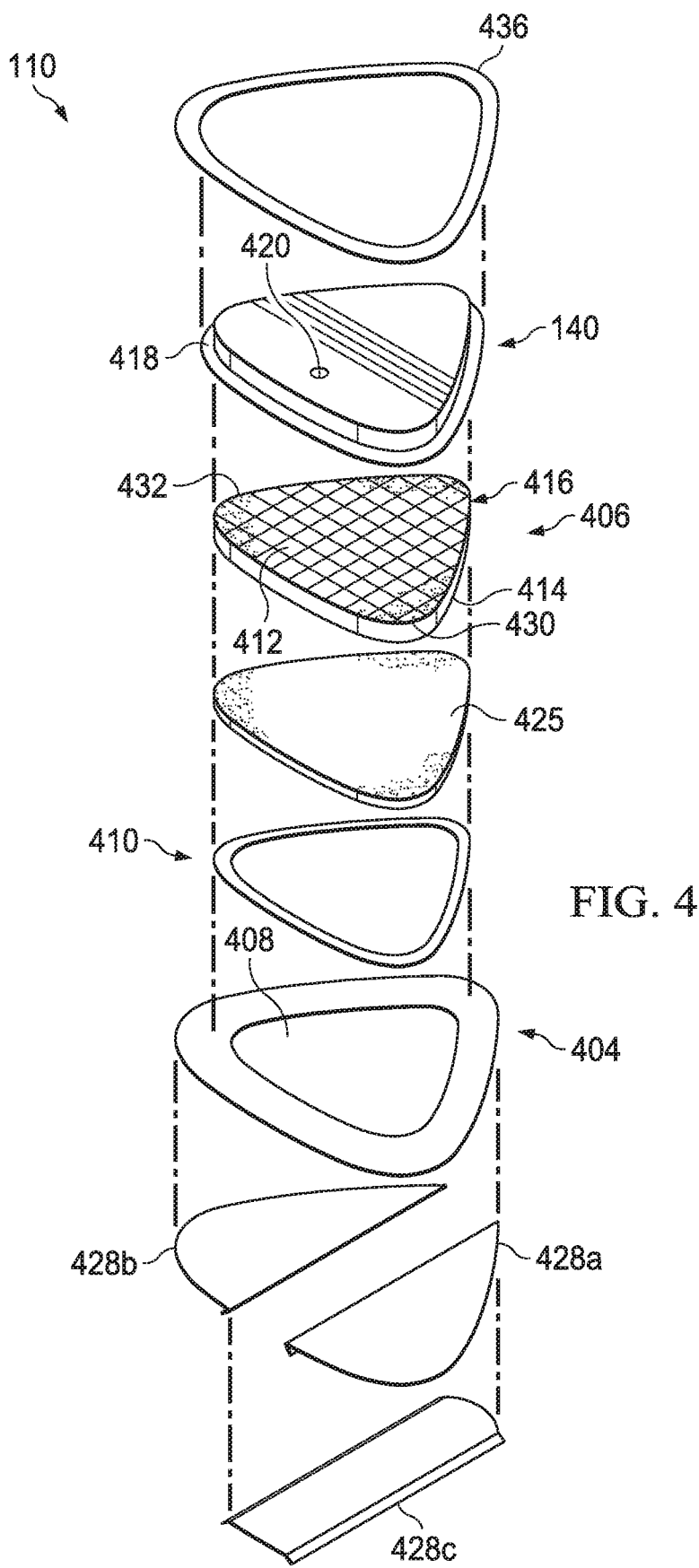
FIG. 4 is an exploded, isometric view of an example embodiment of a dressing, or portion of a dressing assembly, that may be associated with an example embodiment of the therapy system of FIG. 1.
Figure 5:
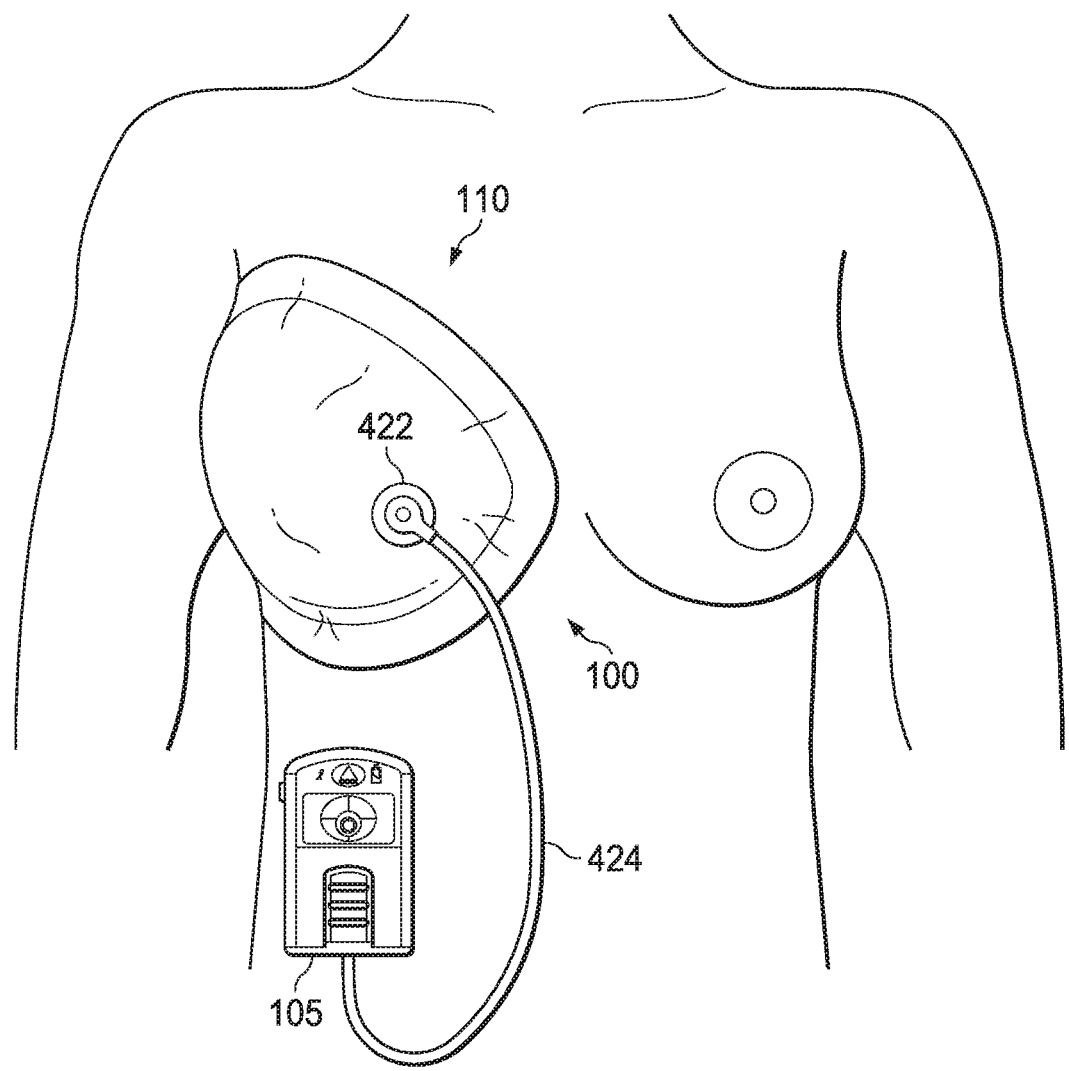
FIG. 5 is a schematic view illustrating an exemplary system having the dressing of FIG. 4 in place on an exemplary tissue site, illustrating additional details that may be associated with some embodiments.

Referring to FIGS. 4-5, the dressing 110 may include features that can treat a tissue site, such as a patient's breast, or parts thereof, and an area of tissue around the tissue/treatment site. For example, the tissue site may be an incision or other treatment target on a patient. The dressing 110 may be configured to treat not only the incision or treatment target, but also, an area of tissue around the incision or treatment target. While the figures may illustrate exemplary dressing embodiments as configured for use on a breast tissue site, other exemplary dressings may have other sizes, shapes, and/or configurations, for example for use on other tissue sites.

FIG. 4 is an exploded, isometric view of an example embodiment of a dressing that may be associated with an example embodiment of the therapy system of FIG. 1. Referring more specifically to FIG. 4, in some examples, the dressing 110 may include an attachment device 404, a manifold 406, and the cover 140. Some examples of the attachment device 404 and other components may include a treatment aperture 408, and the manifold 406 may be configured to be at least partially exposed to a tissue site through the treatment aperture 408. Further, in some examples, the dressing 110 may optionally include an adhesive ring 410 that may be configured to bond a peripheral portion of the manifold 406 to a portion of the attachment device 404. In some examples, the adhesive ring 410 may be formed as part of the attachment device 404, or the adhesive ring 410 may be omitted with the attachment device 404 instead being coupled to the manifold 406 and/or cover 140 with another medically acceptable coupling apparatus. In some examples, the cover 140, the manifold 406, the optional adhesive ring 410, and the attachment device 404 may have similar shapes. The attachment device 404 may be slightly larger than the manifold 406 to permit coupling of the attachment device 404 to the cover 140 around the manifold 406. In some examples, an adhesive may be disposed on a portion of the manifold 406 exposed through the treatment aperture 408. In some embodiments, the adhesive may be pattern-coated, and may cover up to 50% of the exposed portion or surface of the manifold 406.

The cover 140, the manifold 406, the attachment device 404, or various combinations may be assembled before application or at a tissue site. In some embodiments, the dressing 110 may be provided as a single unit.

The manifold 406 may include a first surface 412 and an opposing second surface 414. In some examples, at least a portion of the second surface 414 (e.g. the tissue-facing surface) of the manifold 406 may be configured to face the tissue site (e.g. the area of tissue around the extremity) through the treatment aperture 408. In some examples, the attachment device 404 may be positioned on or at a portion of the second surface 414 of the manifold 406. In some examples, the manifold 406 may include or be formed of a porous material, such as foam.

In some examples, the attachment device 404 may be configured to create a sealed space between the cover 140 and the tissue site, and the manifold 406 may be configured to be positioned in the sealed space. For example, the attachment device 404 may be positioned around an edge 416 of the manifold 406 and configured to surround the tissue site. The cover 140 may be disposed over the manifold 406 and coupled to the attachment device 404 around the manifold 406. For example, the cover 140 may be coupled to a portion of the attachment device 404 extending outward from the edge 416 of the manifold 406. Further, the cover 140 may be larger than the manifold 406, as illustrated in the example of FIG. 4, and may have a perimeter or a flange 418 configured to be attached to the attachment device 404. Assembled, the cover 140 may be disposed over the first surface 412 (e.g. the outward-facing surface) of the manifold 406, and the flange 418 may be attached to the attachment device 404 around the manifold 406. For example, an adhesive may be used to adhere the flange 418 to the attachment device 404, or the flange 418 may be, without limitation, welded, stitched, or stapled to the attachment device 404. In some embodiments, the attachment device may comprise an adhesive applied to the flange 418 and configured to allow attachment of the flange 418 to the tissue site. The cover 140 may also include a port 420 configured to allow fluid communication between the manifold 404 and a dressing interface 422 and/or a fluid conductor 424 (e.g. to apply negative pressure under the cover) as described herein.

The attachment device 404 may take many forms. In some examples, the attachment device 404 may include or be formed of a film or membrane that can provide a seal in a therapeutic negative-pressure environment. In some example embodiments, the attachment device 404 may be a polymer film, such as a polyurethane film, that is permeable to water vapor but impermeable to liquid. The attachment device 404 may have a thickness in the range of 25-50 microns. For permeable materials, the permeability may be low enough that a desired reduced pressure may be maintained. The attachment device 404 may also include a medically-acceptable adhesive, such as a pressure-sensitive adhesive. In examples, the attachment device 404 may be a polymer film coated with an adhesive, such as an acrylic adhesive, which may have a coating weight between 25-65 grams per square meter (g.s.m.). Thicker adhesives, or combinations of adhesives, may be applied in some examples to improve the seal and reduce leaks.

In some examples, the attachment device 404 may include or be formed of a hydrocolloid. In some examples, the attachment device 404 may be configured or referred to as a sealing ring or a gasket member. In other examples, the dressing 110 may include a gasket member (not shown) in addition to the attachment device 404. In such an example, the gasket member may be a peripheral member, such as a hydrocolloid ring, and at least a portion of the attachment device 404 may be positioned between the manifold 406 and the gasket member on or at a surface of the manifold 406, such as the second surface 414, configured to face the area of tissue around the tissue site. In some examples, the gasket member may have a similar or analogous shape as the adhesive ring 410, but the gasket member may be positioned on a surface of the attachment device 404 configured to face the tissue site such that the gasket member is configured to be positioned between the tissue site and the attachment device 404.

In some examples, the dressing 110 may optionally further include a tissue contact layer 425, which may be coupled to a surface of the manifold 406, such as the second surface 414, and may be configured to be exposed to the tissue site. In some embodiments, the tissue contact layer 425 may be configured to be positioned in direct contact with the tissue site, for example forming a tissue-contact surface. In other embodiments (e.g. without a tissue-contact layer), the tissue-contact surface may be formed by the manifold and/or the attachment device. The tissue contact layer 425 may include or be formed of a material that substantially reduces or eliminates skin irritation while allowing fluid transfer through the tissue contact layer. In some embodiments, the tissue contact layer 425 may form a fluid control layer, configured to allow fluid communication between the tissue site and the manifold during negative-pressure therapy, while minimizing backflow of fluids (such as exudate) from the manifold to the tissue site (e.g. to minimize maceration). In some examples, the tissue contact layer 425 may include or be formed of one or more of the following materials, without limitation: a woven material, a non-woven material, a polyester knit material, and a fenestrated film.

In some examples, the attachment device 404, which may comprise an adhesive on a surface of the dressing 110 configured to face the tissue site (e.g. on the tissue-contact surface), may be covered by one or more release liners 428 prior to applying the dressing 110 at the tissue site. For example, as shown in FIG. 4, the dressing 110 may include a first release liner 428a, a second release liner 428b, and a third release liner 428c. The first release liner 428a may be positioned proximate to a first side 430 of the manifold 406 or the dressing 110, the second release liner 428b may be positioned proximate to a second side 432 of the manifold 406 or the dressing 110 (e.g. with the first side 430 and the second side 432 opposite each other across a line of symmetry), and the third release liner 428c may be positioned proximate to a fold axis, centerline, or line or symmetry of the manifold 406 or the dressing 110 (e.g. spanning a central portion of the manifold and/or dressing). The central portion with the line of symmetry may be located between the first side 430 and the second side 432, and the third release liner 428c may be positioned between the first release liner 428a and the second release liner 428b. In some examples, the third release liner 428c may be configured to be removed to expose an adhesive or portion of the attachment device 404 proximate to the line of symmetry prior to removal of the first release liner 428a and the second release liner 428b. Such a configuration may permit the central portion of the dressing 110 (e.g. in proximity to the line of symmetry) to be initially positioned or aligned at a tissue site, such as the extremity, while the first release liner 428a and the second release liner 428b protect other portions of the adhesive or the attachment device 404. For example, a portion of the third release liner 428c may cover or be positioned over a portion of the first release liner 428a and/or the second release liner 428b such that the third release liner 428c may be removed prior to removal of the first release liner 428a and the second release liner 428b. In some examples, the dressing 110 may have two release liners, each of which may have perforations or slits (not shown here) configured to allow the release liners to be separated into smaller pieces for removal. Additionally, some embodiments may also have one or more casting sheet liners 436.

Additionally or alternatively, the first release liner 428a, the second release liner 428b, and the third release liner 428c may provide stiffness to the attachment device 404 to facilitate handling and application. Additionally or alternatively, the casting sheet liners 436 may cover the flange 418 to provide stiffness to the cover 140 for handling and application. The one or more release liner 428 may be configured to releasably cover the attachment device 404, for example to protect and maintain the adhesive of the attachment device 404 until the time of application of the dressing 110 to the tissue site.

In some examples, the dressing 110 may include the dressing interface 422, which may be fluidly coupled to the manifold 406 through the port 420 in the cover 140. In some embodiments, the dressing interface 422 may be coupled in the central portion of the manifold 406 (e.g. in proximity to the line of symmetry), and may be configured to be coupled to the negative-pressure source through, for example, the fluid conductor 424, conduit, or tube coupled in fluid communication between the dressing interface 422 and the reduced pressure source 105.

FIG. 5 is a schematic view illustrating an exemplary system having the dressing 110 of FIG. 4 in place on an exemplary tissue site, illustrating additional details that may be associated with some embodiments. The system 100 may comprise a negative-pressure source 105 in fluid communication with the dressing 110. For example, the dressing 110 may comprise a dressing interface 422, which may penetrate the cover of the dressing 110 to fluidly couple to the manifold of the dressing 110, and a fluid conductor 424 may fluidly couple the negative-pressure source 105 to the dressing interface 422 (thereby fluidly coupling the negative-pressure source 105 to the manifold of the dressing 110, for application of negative-pressure therapy to the tissue site through the manifold of the dressing 110). In FIG. 5, the tissue site is shown as a breast of a patient, and the dressing 110 may be coupled to the breast.

In operation, the negative-pressure source 105 can reduce pressure in the sealed therapeutic environment (e.g. when the dressing 110 is applied to the tissue site in the usage configuration). Reduced pressure applied to the tissue site through the manifold 406 in the sealed therapeutic environment can induce macro-strain and micro-strain in the tissue site, as well as remove exudates and other fluids from the tissue site, which can be collected in the container 115.

In general, exudates and other fluids flow toward lower pressure along a fluid path. Thus, the term "downstream" may refer to a location in a fluid path relatively closer to a source of reduced pressure or further away from a source of positive pressure. Conversely, the term "upstream" may refer to a location further away from a source of reduced pressure or closer to a source of positive pressure.

In some example embodiments, the controller 120 may receive and process data from one or more sensors, such as the first sensor 125. The controller 120 may also control the operation of one or more components of the therapy system 100 to manage the pressure delivered to the tissue interface 135, such as the manifold 406 and associated components. In some embodiments, the controller 120 may include an input for receiving a desired target pressure, and may be programmed for processing data relating to the setting and inputting of the target pressure to be applied to the tissue interface 135. In some example embodiments, the target pressure may be a fixed pressure value set by an operator as the target reduced pressure desired for therapy at a tissue site and then provided as input to the controller 120. The target pressure may vary from tissue site to tissue site based on the type of tissue forming a tissue site, the type of injury or wound (if any), the medical condition of the patient, and the preference of the attending physician. After selecting a desired target pressure, the controller 120 can operate the negative-pressure source 105 in one or more control modes based on the target pressure, and may receive feedback from one or more sensors to maintain the target pressure at the tissue interface 135. In some embodiments, the manifold 406 may have distinct pressure zones, and different target pressures and control modes may be applied to different pressure zones.

Some dressing 110 embodiments may be configured to provide multiple, different pressure zones to a tissue site. For example, some dressing 110 embodiments may have two zones: a negative-pressure zone, and an isolated zone (such as a zone of ambient pressure). The two zones may be fluidly isolated from each other, with no fluid communication therebetween. In some embodiments, the negative-pressure zone may be configured to surround the isolated zone on the tissue site. In some embodiments, the isolated zone may be configured to lie within (e.g. underlie) the negative-pressure zone (e.g. located between a portion of the tissue site and the negative-pressure zone). The negative-pressure zone may be configured to provide negative-pressure therapy to the tissue site. The isolated zone may be configured to have a pressure different than that of the negative-pressure zone. For example, the isolated zone may be configured to shield a portion of the tissue site from the negative pressure and/or to maintain ambient pressure at the portion of the tissue site. In addition to maintaining ambient pressure and/or blocking the negative-pressure while surrounded by the negative-pressure zone, the isolated zone may also be configured to resist appositional and/or decompressive forces resulting from the negative pressure in the negative-pressure zone during negative-pressure therapy.

Figure 6:
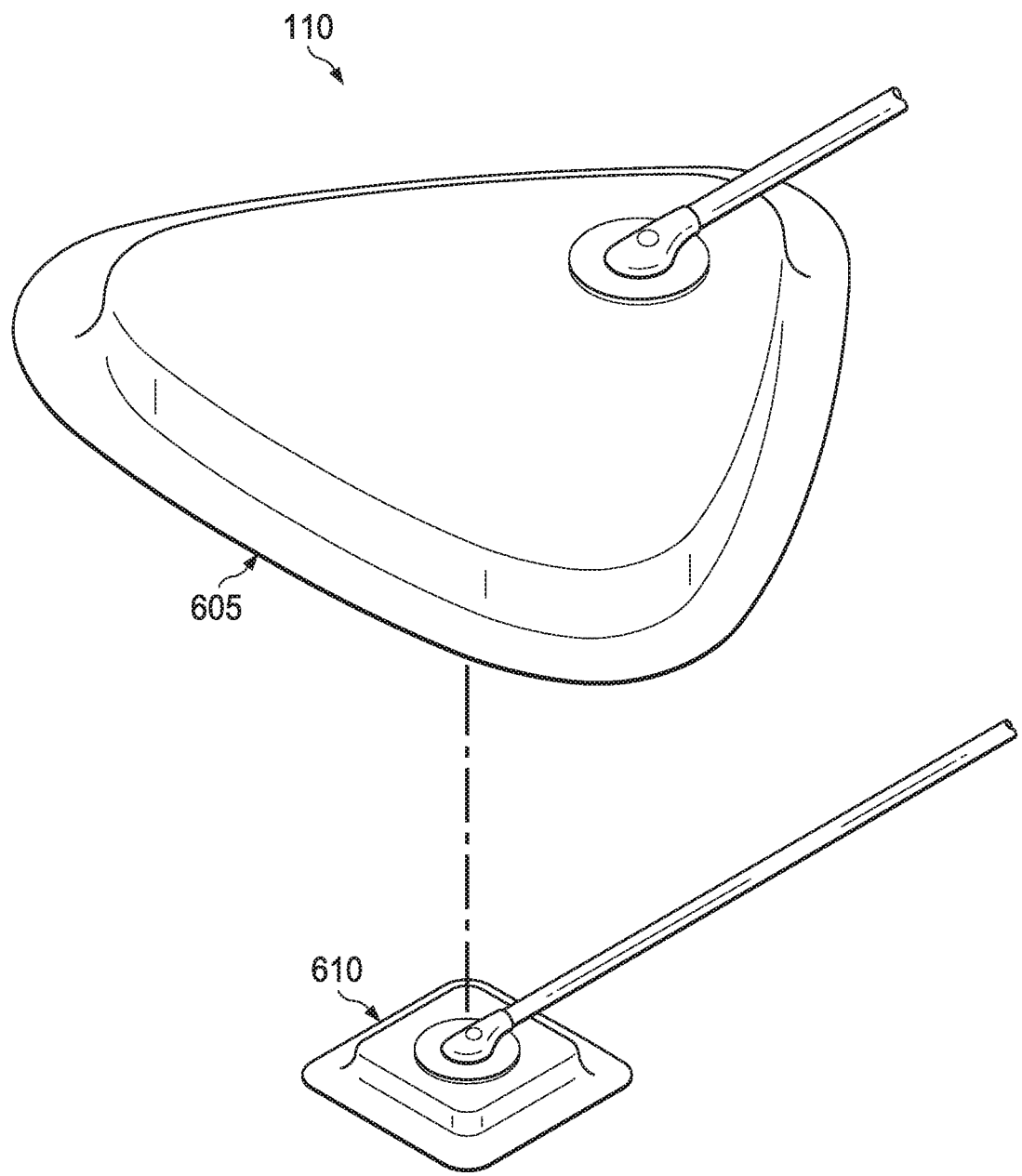
FIG. 6 is an exploded, isometric view of another example embodiment of a dressing (e.g. a dressing assembly, with a negative-pressure dressing and an isolation patch) that may be associated with an example embodiment of the therapy system of FIG. 1.

FIG. 6 is an exploded, isometric view of another example embodiment of a dressing 110 that may be associated with an example embodiment of the therapy system of FIG. 1. The dressing 110 of FIG. 6 may be configured with two exemplary pressure zones. In some embodiments, the dressing 110 of FIG. 6 may comprise two parts: a negative-pressure dressing 605 and an isolation patch 610, such as a zone of ambient pressure (ZAP) patch. The negative-pressure dressing 605 may be configured to form the negative-pressure zone (e.g. when attached to the tissue site), and the isolation patch 610 may be configured to form the isolated zone (e.g. when attached to a portion of the tissue site and/or under the negative-pressure dressing). In some embodiments, the two-part dressing 110 may form a dressing assembly. In some embodiments, the negative-pressure dressing 605 may be similar to the dressing in FIG. 4, and may be configured to overlie the isolation patch 610. In use, the isolation patch 610 may be configured to underlie the negative-pressure dressing 605, for example located between the portion of the tissue site and the negative-pressure dressing 605. When used together as a dressing assembly, the negative-pressure dressing 605 and the isolation patch 610 may allow for application of negative-pressure therapy to a tissue site generally, except for a portion of the tissue site (covered by the isolation patch 610) which may be isolated and/or shielded from the negative pressure. In some embodiments, the isolation patch 610 may be configured to isolate the portion of the tissue site from the negative pressure of the negative-pressure zone, to prevent infiltration of the negative pressure from the negative-pressure zone into the isolated zone formed by the isolated patch 610 on the portion of the tissue site, to prevent fluid communication between the isolated zone and the negative-pressure zone, to maintain ambient pressure at the portion of the tissue site, to prevent or minimize pressure changes at the portion of the tissue site covered by the isolation patch 610, to allow a pressure different than that of the negative-pressure zone to be applied to or maintained at the portion of the tissue site in the isolated zone, and/or to exclude the negative pressure from the portion of the tissue site. In some embodiments, the isolation patch 610 may be configured to resist, reduce, and/or minimize appositional and/or decompressive forces (e.g. from negative-pressure therapy under the negative-pressure dressing 605) on the portion of the tissue site.

Figure 7:
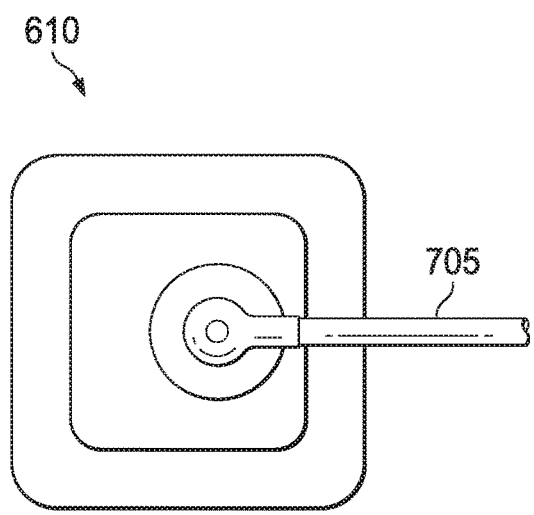
FIG. 7 is a top plan view of the isolation patch portion of the dressing of FIG. 6, illustrating additional details that may be associated with some embodiments.

FIG. 7 is a top plan view of the isolation patch 610 portion of the dressing of FIG. 6, illustrating additional details that may be associated with some embodiments. As shown in FIG. 7, the isolation patch 610 may be vented, for example with a ventilation conduit 705 configured to fluidly couple the isolation patch 610 to an ambient environment outside of the negative-pressure dressing. The vent of the isolation patch 610 may be configured to fluidly couple the isolation patch 610 (e.g. a patch manifold) to the ambient environment. In some embodiments, the isolation patch 610 may have a length of 13 cm or less. In some embodiments, the isolation patch 610 may be sized approximately 2 cm by 2 cm or have a diameter of approximately 2 cm. In some embodiments, the isolation patch 610 may have dimensions (e.g. length and width, or diameter) from approximately 2 cm-5 cm, 2 cm-4 cm, or 2 cm-3 cm. In some embodiments, the negative-pressure dressing 605 may have dimensions of approximately 21 cm by 19 cm, 24 cm by 22 cm, or 29 cm by 27 cm. In some embodiments, the ratio of the surface area of the negative-pressure dressing 605 to the surface area of the isolation patch 610 may be from about 40:1 to 132:1.

Figure 8:
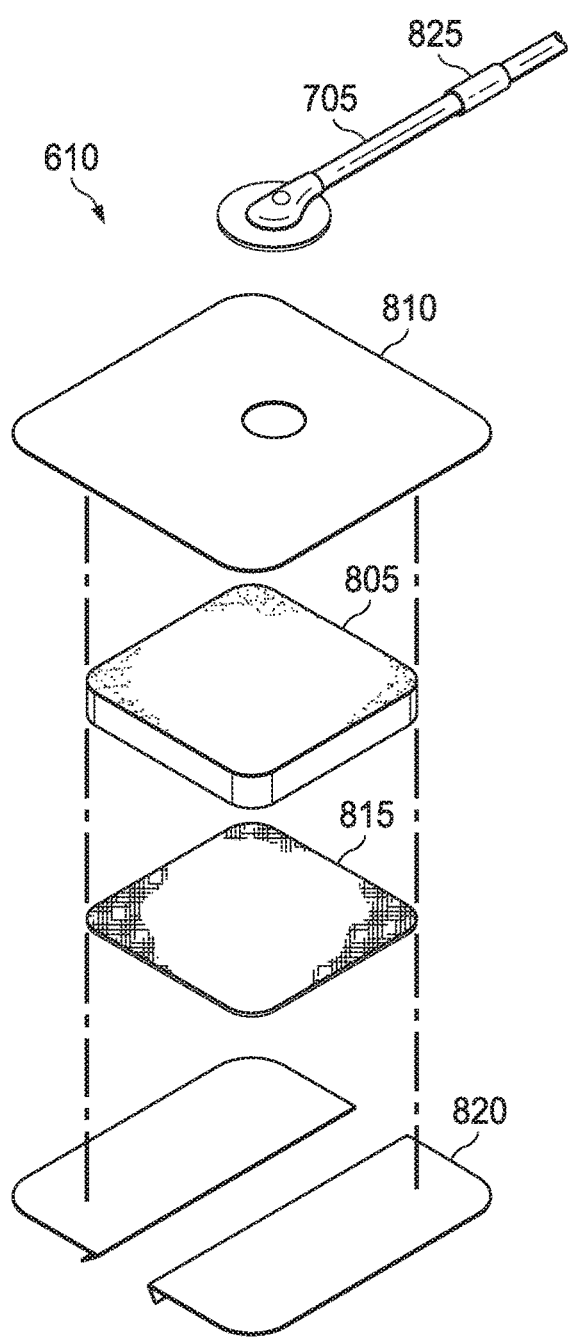
FIG. 8 is an exploded isometric view of the isolation patch of FIG. 7, illustrating additional details that may be associated with some embodiments.

FIG. 8 is an exploded isometric view of the isolation patch 610 of FIG. 7, illustrating additional details that may be associated with some embodiments. In some embodiments, the isolation patch 610 may comprise or consist essentially of a force-dissipating pad, which may be configured to dissipate or isolate the portion of the tissue site from forces that may be associated with the negative pressure, such as appositional, compressive, or contractive forces for example. For example, the force-dissipating pad in FIG. 8 may comprise a patch manifold 805. In some embodiments, the patch manifold 805 may be similar to the manifold 406 described above (e.g. of the negative-pressure dressing). In some embodiments, the patch manifold 805 may comprise open-cell and/or reticulated foam, such as polyurethane foam. The patch manifold 805 may have a thickness of about 5-10 mm, in some embodiments, for example about 5 mm, about 7 mm, or about 10 mm. The isolation patch 610 may also comprise a patch cover 810, which may be configured to be disposed over the patch manifold 805 (e.g. opposite the tissue site) and which may be formed of material that substantially prevents and/or restricts fluid flow therethrough and/or provides a fluid seal adequate to maintain a reduced pressure at the tissue site for a given negative-pressure source. For example, the patch cover 810 may be occlusive. In some embodiments, the patch cover 810 may also have a high MVTR, such as greater than 240 g/m$^2$/24 hours. In some embodiments, the patch cover 810 may be similar to the cover 140 described above (e.g. with respect to the negative-pressure dressing). In some embodiments, the patch cover may comprise polyurethane film. The patch cover 810 may comprise a vent opening, in some embodiments, allowing fluid communication between the ventilation conduit 705 and the patch manifold 805, but may otherwise be configured to prevent fluid flow therethrough. In some embodiments, the patch cover 810 may be coupled to the patch manifold 805 (e.g. on an outward-facing side of the patch manifold 805) and/or may form an outer surface of the isolation patch 610. Some embodiments of the isolation patch 610 may further comprise an optional patch tissue contact layer 815 (e.g. similar to the tissue contact layer 425 which may be used for the negative-pressure dressing). The patch tissue contact layer 815 may be coupled to the patch manifold 805, for example opposite the patch cover 810, in some embodiments, and/or may be configured to allow fluid communication from the tissue site to the patch manifold 805. In some embodiments, the patch tissue contact layer 815 may form the tissue-contact surface of the isolation patch 610, configured to directly contact the portion of the tissue site. In some embodiments, the patch tissue contact layer 815 may comprise one or more of the following: a woven material, a non-woven material, a polyester knit material, and a fenestrated film. Some embodiments of the isolation patch 610 may further comprise a patch attachment device (not shown here, which may be similar to the attachment device of the negative-pressure dressing 605), which may be configured to attach the patch cover 810 to the isolated portion of the tissue site (e.g. located around the inward-facing surface of the patch manifold 805 and/or the patch tissue contact layer 815 of the isolation patch) and to form a seal around the perimeter of the portion of the tissue site, preventing fluid communication between the isolated portion of the tissue site and the negative-pressure zone under the negative-pressure dressing. Some embodiments of the isolation patch 610 may further comprise one or more patch release liner 820 (e.g. similar to the release liner(s) 428 for the negative-pressure dressing), which may releasably cover the patch attachment device of the isolation patch. In some embodiments, a separate patch release liner 820 may releasably cover the patch attachment device, and one or more separate dressing release liners 428 may cover the attachment device for the negative-pressure dressing 605. In other embodiments, one or more release liner 428 may cover both the patch attachment device and the attachment device for the negative-pressure dressing 605 (e.g. the patch release liner may be integrated into the one or more release liners for the negative-pressure dressing 605).

In some embodiments, the ventilation conduit 705 may comprise a proximal end configured to be fluidly coupled to the vent opening of the isolation patch 610, and a distal end configured to be positioned external to the negative-pressure dressing 605. In some embodiments, the proximal end of the ventilation conduit 705 may be in fluid communication with the patch manifold 805 through the patch cover 810. In some embodiments, the ventilation conduit 705 may comprise a filter 825, which may be positioned in-line (e.g. in the passage of the conduit, between the distal end and the proximal end) and/or configured to filter airflow from the ambient environment to the isolation patch 610. In some embodiments, the filter 825 may comprise one or more of the following: a bacterial filter, a hydrophobic filter, and a charcoal filter. In some embodiments, the ventilation conduit 705 may be configured to resist collapse under negative-pressure therapy, for example being sufficiently rigid to resist full compression and/or to maintain an open pathway when in use. In some embodiments, the vent between the isolation patch 610 and the ambient environment may be sized sufficiently to maintain ambient pressure within the isolated zone during negative-pressure therapy. For example, the vent may be sized with a flow rate of about 5 mL/minute or greater than 5 mL/minute in some embodiments.

Figure 9:
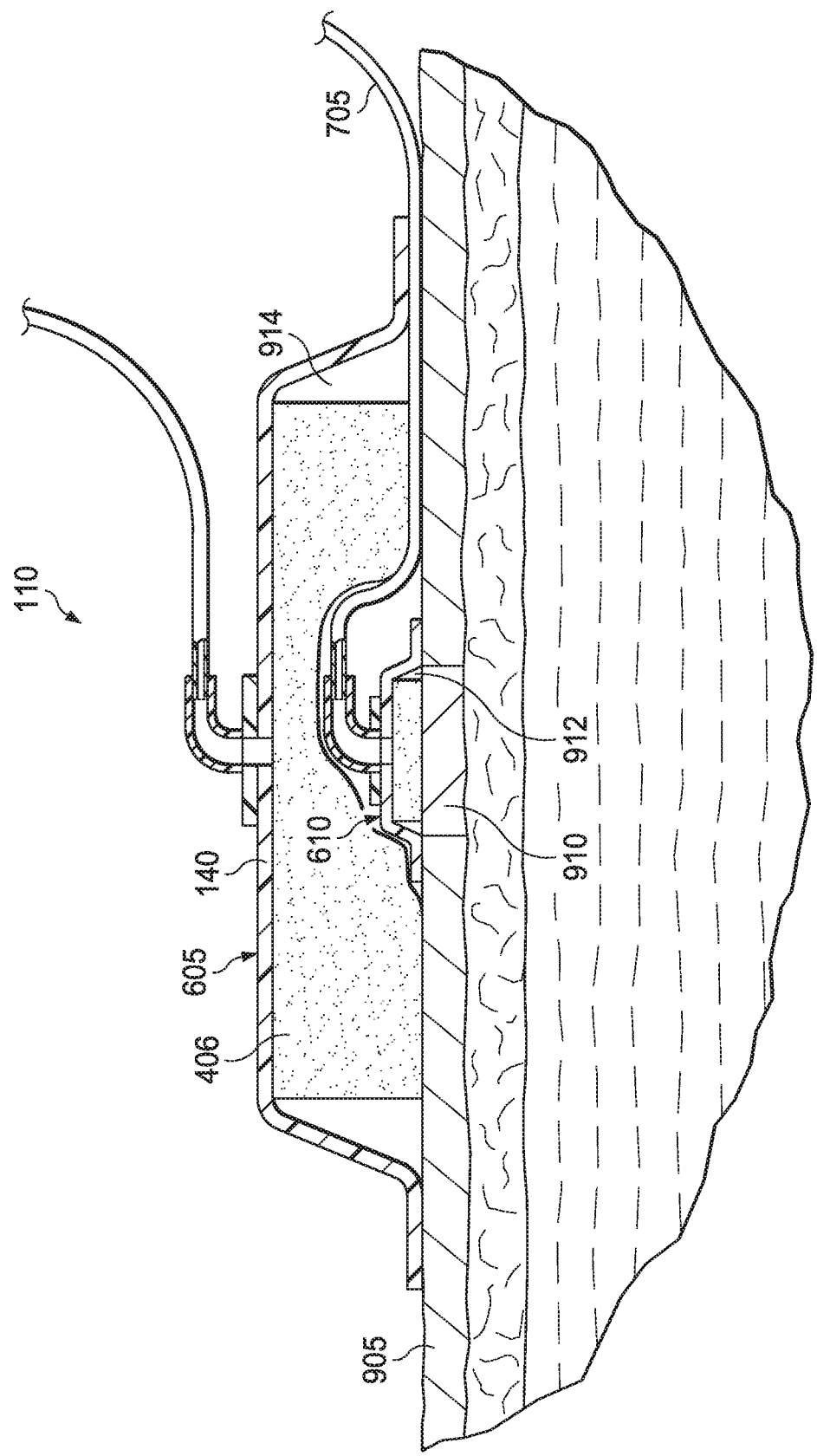
FIG. 9 is a schematic cross-section view of the dressing of FIG. 6 in place on an exemplary tissue site, illustrating additional details that may be associated with some embodiments.

FIG. 9 is a schematic cross-section view of the dressing 110 of FIG. 6 in place on an exemplary tissue site 905, illustrating additional details that may be associated with some embodiments. The isolation patch 610 may cover the portion of the tissue site 910 which is to be isolated (e.g. shielded from negative pressure and/or maintained at ambient pressure), forming a first sealed space 912 (which may form the isolated zone and/or zone of ambient pressure). The negative-pressure dressing 605 may cover the isolation patch 610 and the tissue site 905, forming a second sealed space 914 (which may form the negative-pressure zone). For example, the negative-pressure dressing 605 may be coupled over the tissue site 905, with the isolation patch 610 located thereunder. The isolation patch 610 may be located between the portion of the tissue site 910 and the negative-pressure dressing 605, with the negative-pressure dressing 605 surrounding the isolation patch 610. In some embodiments, the first sealed space 912 may be located within the second sealed space 914, and the first sealed space 912 may be isolated from the second sealed space 914 (e.g. with substantially no fluid communication therebetween). In some embodiments, the manifold 406 for the negative-pressure dressing 605 may be located between the isolation patch 610 and the cover 140 for the negative-pressure dressing 605. In some embodiments, a portion of the manifold 405 located over the isolation patch 610 may be compressed (e.g. to form a space within the negative-pressure dressing 605 for the isolation patch 610), while other embodiments of the manifold 406 may comprise a cavity (not shown, but located to open on the inward-facing surface of the manifold) configured to receive the isolation patch 610. In some embodiments, the isolation patch 610 may be attached to the negative-pressure dressing 605 (e.g. coupled to the manifold 406), for example forming a unitary dressing assembly. In other embodiments, the isolation patch 610 may initially be separate from the negative-pressure dressing 605, for example allowing placement of the isolation patch 610 first, before placement of the negative-pressure dressing 605.

In some embodiments, the ventilation conduit 705 of the isolation patch 610 may extend out from under the negative-pressure dressing 605, with the distal end of the ventilation conduit located external to the negative-pressure dressing 605. For example, the ventilation conduit 705 may extend between the manifold 406 of the negative-pressure dressing 605 and the tissue site 905, out beyond the perimeter of the negative-pressure dressing 605 where the cover 140 attaches to the tissue site 905. The attachment device may seal the cover 140 of the negative-pressure dressing 605 around the ventilation conduit 705, preventing any substantial leakage at the location where the ventilation conduit 705 exits from under the negative-pressure dressing 605 at the perimeter of the negative-pressure dressing 605.

Figure 10:
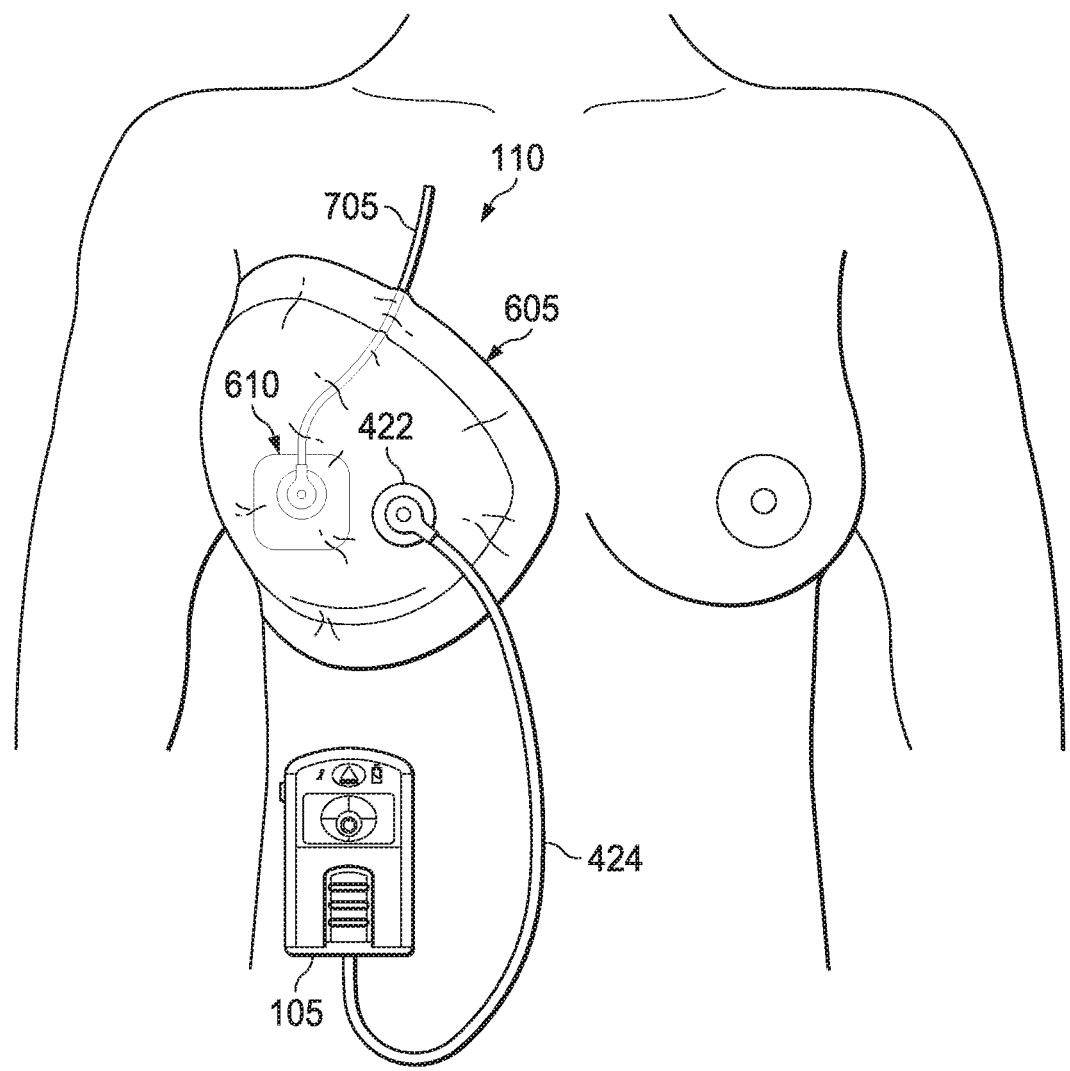
FIG. 10 is a schematic view illustrating an exemplary system having the dressing of FIG. 6 in place on an exemplary tissue site, illustrating additional details that may be associated with some embodiments.

FIG. 10 is a schematic view illustrating an exemplary system having the dressing 110 of FIG. 6 in place on an exemplary tissue site, illustrating additional details that may be associated with some embodiments. As shown in FIG. 10, the isolation patch 610 may underlie the negative-pressure dressing 605, while the negative-pressure dressing 605 is on the tissue site. The negative-pressure dressing 605 may cover and seal the tissue site for negative-pressure therapy, and the isolation patch 610 may cover and seal the portion of the tissue site (to be shielded from negative pressure). The ventilation conduit 705 may extend out from the isolation patch 610, beyond the negative-pressure dressing 605, to provide fluid communication between the isolation patch 610 and the ambient environment. Fluid communication with the ambient environment may ensure that the isolation patch 610 maintains ambient pressure within the first sealed space. The negative-pressure source 105 may be fluidly coupled to the negative-pressure dressing 605. For example, the fluid conductor 424 may fluidly couple the negative-pressure source 105 to the dressing interface 422 of the negative-pressure dressing 605. The negative-pressure source 105 may be configured to provide negative pressure to the second sealed space of the negative-pressure dressing 605, thereby providing negative-pressure therapy to the tissue site. The isolation patch 610 may shield the portion of the tissue site underlying the isolation patch 610 from negative pressure, for example with the first sealed space providing and/or maintaining ambient pressure to the portion of the tissue site (despite the application of negative-pressure in the second sealed space surrounding the isolation patch 610). In some embodiments, the isolation patch 610 may also (e.g. simultaneously) shield the portion of the tissue site from appositional and/or decompressive forces which may be caused by the negative-pressure therapy within the negative-pressure dressing 605.

In FIG. 10, the isolation patch 610 may cover the nipple of the patient (e.g. the portion of the tissue site may comprise a nipple), and the negative-pressure dressing 605 may cover a breast of the patient (e.g. the tissue site may comprise the breast). Application of negative pressure from the negative-pressure source 105 may provide negative-pressure therapy to the breast tissue site through the negative-pressure dressing 605, except for the nipple portion of the tissue site (which may experience ambient pressure and/or may not experience substantial appositional and/or decompressive forces under the isolation patch 610).

While FIG. 10 illustrates the dressing on a breast tissue site, with the isolation patch over the nipple portion of the tissue site, other dressing embodiments may be configured for use on different tissue sites. For example, some dressing embodiments may have an isolation patch configured for use over a genital region. Some dressing embodiments may be configured for use with colorectal surgery. Some dressing embodiments may have an isolation patch configured to cover compromised vascular structures. A two-zone dressing may be useful anytime the tissue site generally may benefit from negative-pressure wound therapy, but also includes a portion of the tissue site that may not be suitable or recommended for negative-pressure wound therapy.

Figure 11:
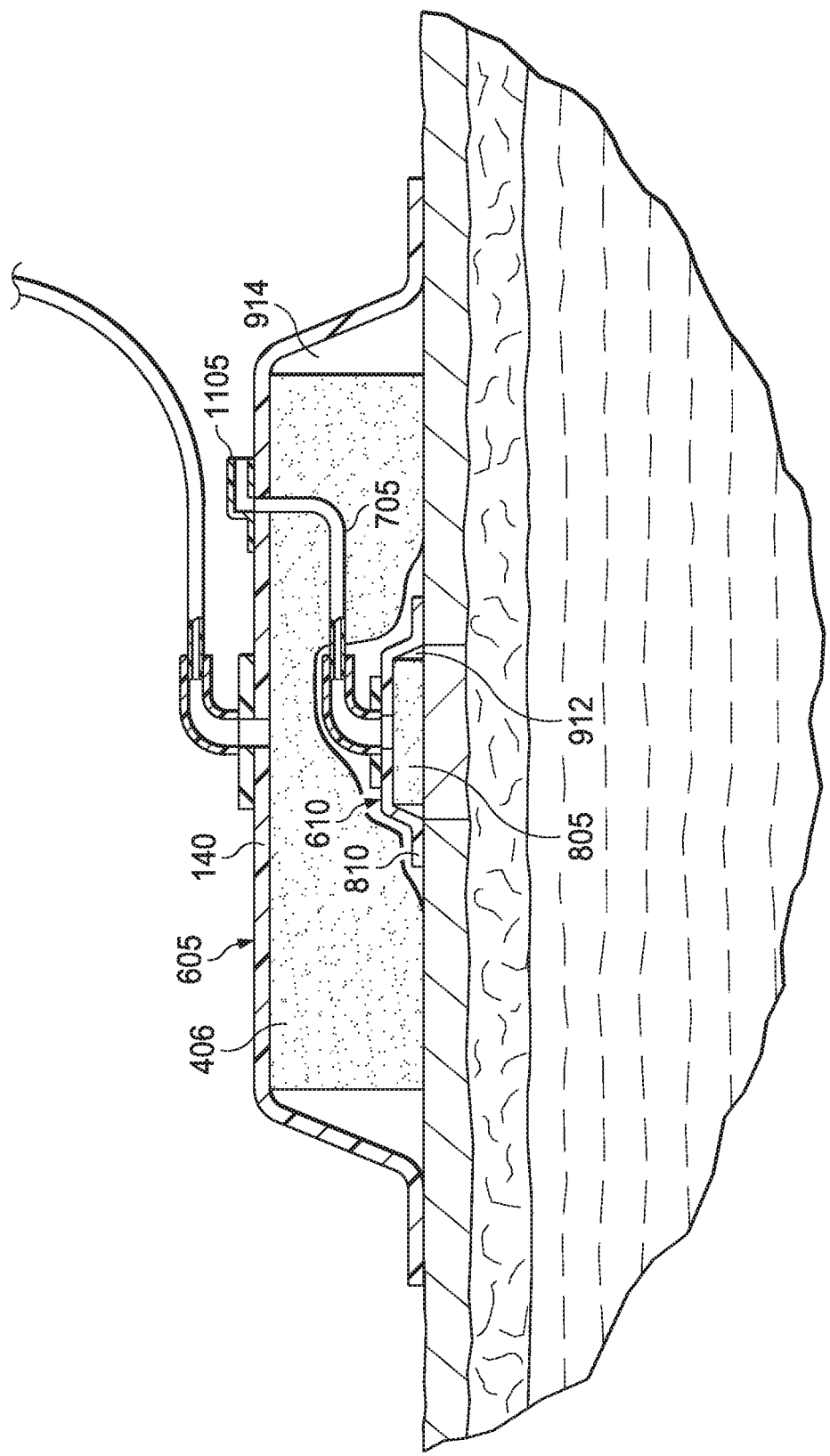
FIG. 11 is a schematic cross-section view of yet another example embodiment of a dressing (e.g. a dressing assembly, with a negative-pressure dressing and an isolation patch) that may be associated with an example embodiment of the therapy system of FIG. 1.

FIG. 11 is a schematic cross-section view of yet another example embodiment of a dressing 110 that may be associated with an example embodiment of the therapy system of FIG. 1. The dressing 110 of FIG. 11 may be similar to that of FIG. 9, but may be configured to vent the isolation patch 610 (e.g. the first sealed space 912) through the cover 140 of the negative-pressure dressing 605. For example, the ventilation conduit 705 may fluidly couple from the isolation patch 610 to the ambient environment through the cover 140 of the negative-pressure dressing 605. In some embodiments, the cover 140 may comprise a ventilation port 1105, allowing the vent to penetrate the cover 140, and the distal end of the ventilation conduit 705 may be fluidly coupled to the ambient environment outside the negative-pressure dressing 605 through the ventilation port 1105. In some embodiments, the ventilation conduit 705 may also penetrate the manifold 406 of the negative-pressure dressing 605. In other embodiments, the ventilation conduit 705 may not penetrate the manifold 406, but rather may extend around the manifold 406 of the negative-pressure dressing 605 (e.g. between the manifold and the cover) to fluidly couple the isolation patch 610 to the ventilation port 1105. In some embodiments, the ventilation port 1105 may be configured to substantially prevent leakage between the ambient environment and the second sealed space 914 within the negative-pressure dressing 605.

Figure 12:
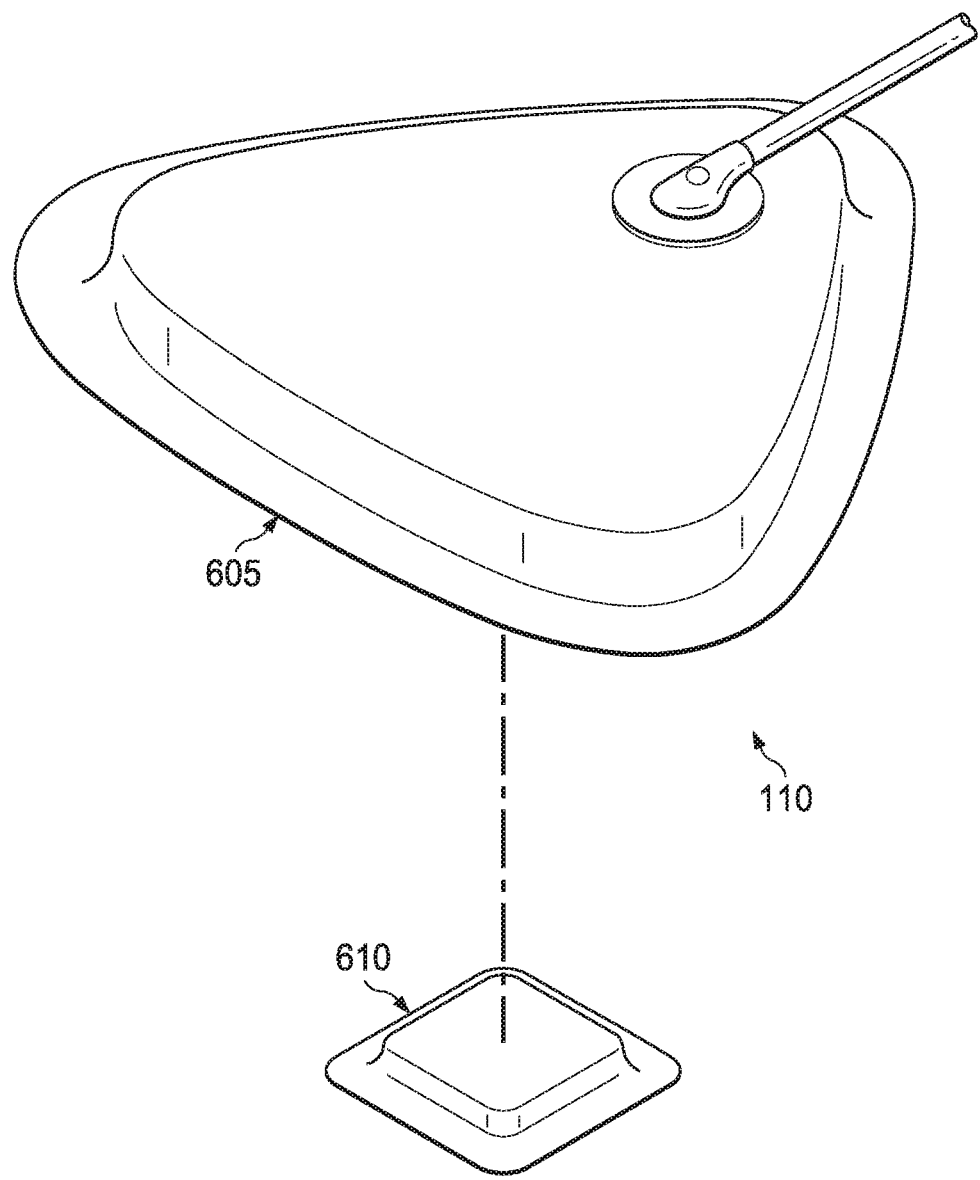
FIG. 12 is an exploded, isometric view of still another example embodiment of a dressing (e.g. a dressing assembly, with a negative-pressure dressing and an unvented isolation patch) that may be associated with an example embodiment of the therapy system of FIG. 1.

FIG. 12 is an exploded, isometric view of still another example embodiment of a dressing 110 (or dressing assembly) that may be associated with an example embodiment of the therapy system of FIG. 1. Dressing 110 of FIG. 12 may be similar to that of FIG. 6, but the isolation patch 610 may be configured to be un-vented (e.g. completely sealed, so as to be sealed to both the negative pressure of the negative-pressure dressing 605 and the ambient environment), without any fluid communication between the isolation patch 610 and the ambient environment. For example, the isolation patch 610 may be configured to seal the portion of the tissue site to block negative pressure and/or to retain ambient pressure, and/or configured to resist or dampen appositional and decompression forces, without having a vent to ambient atmosphere. Thus, the isolation patch 610 of FIG. 12 may have no vent. In some embodiments, the negative-pressure dressing 605 of FIG. 12 may be similar to or identical with that of FIG. 6.

Figure 13:
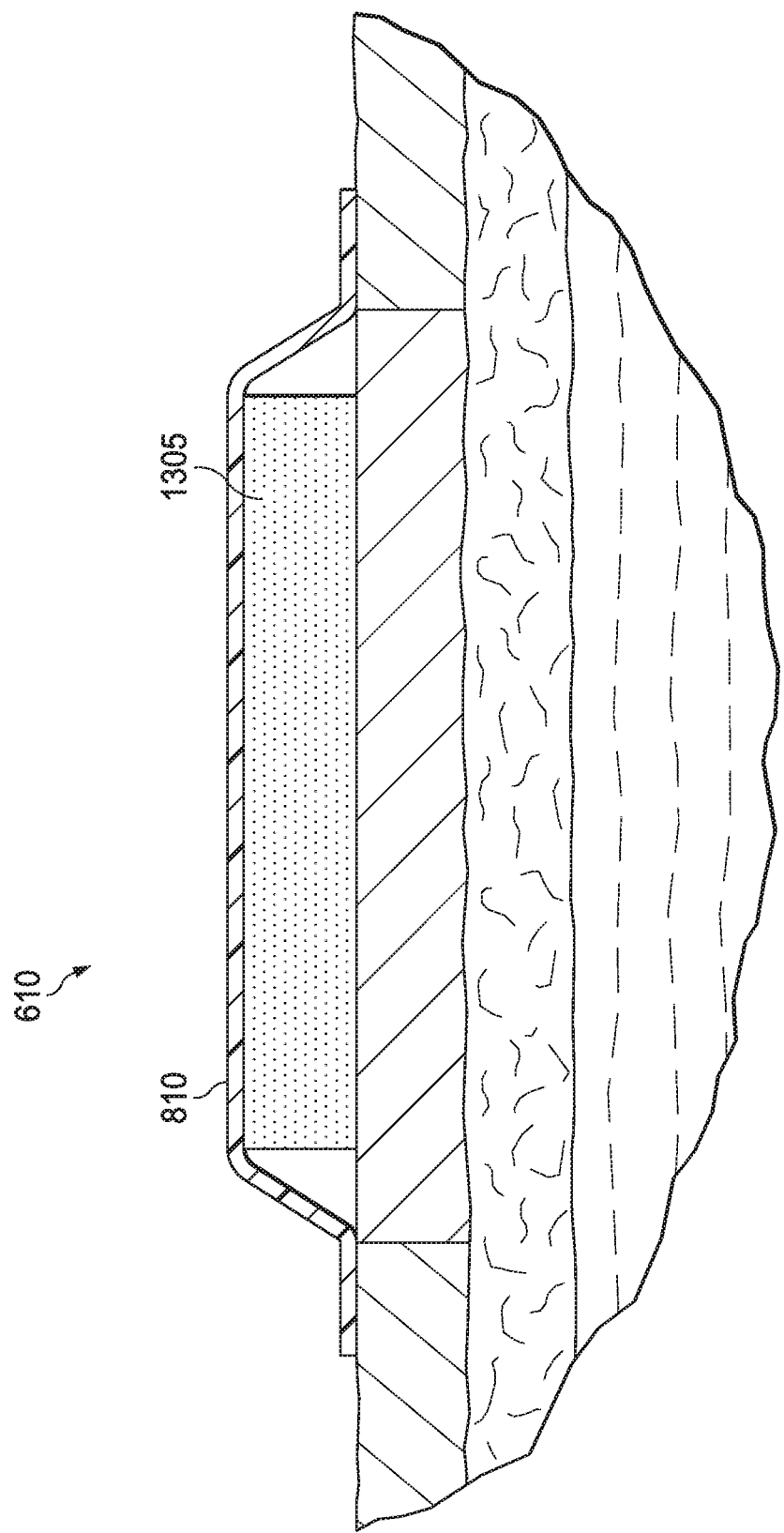
FIG. 13 is a schematic cross-section view of the isolation patch portion of the dressing of FIG. 12, illustrating additional details that may be associated with some embodiments.

FIG. 13 is a schematic cross-section view of the isolation patch 610 portion of the dressing of FIG. 12, illustrating additional details that may be associated with some embodiments. The isolation patch 610 of FIG. 12 may be configured to be unvented (e.g. not vented to the ambient environment). In some embodiments, the isolation patch 610 may comprise or consist essentially of a force-dissipating pad. In FIG. 12, the isolation patch 610 may comprise a force-dissipating pad and a patch cover 810 disposed over the force-dissipating layer to form the outer surface of the isolation patch 610. In some embodiments, the patch cover 810 may be configured to prevent fluid flow therethrough, and may be unvented (e.g. with no openings therethrough). In some embodiments, the patch cover 810 may be occlusive. In some embodiments, the force-dissipating pad may comprise a gel layer 1305, which may be configured to resist appositional and/or decompressive forces arising due to negative-pressure therapy. In some embodiments, the force-dissipating pad, such as gel layer 1305, may be occlusive. For example, the force-dissipating pad may substantially resist airflow so as to be substantially non-existent. In some embodiments, the force-dissipating pad may have low surface roughness, a thickness greater than ⅛ inch, and/or a low durometer (such as 10 or softer on the SHORE 00 scale). In some embodiments, the gel layer 1305 may comprise TPE gel and/or have a thickness of about 5 mm-10 mm. In some embodiments, the force-dissipating pad may comprise one or more other dense materials that are occlusive and/or that resist appositional and/or decompressive forces (e.g. with characteristics similar to the gel layer). For example, the force-dissipating pad may comprise one or more of the following: silicone, rubber with a low durometer, and closed-cell foam. In some embodiments, the isolation patch 610 may further comprise an attachment device (not shown), configured to attach the isolation patch 610 to the portion of the tissue site and to form a seal around the perimeter (e.g. so that the first sealed space/isolated zone/zone of ambient pressure within the isolation patch 610 is completely sealed around the portion of the tissue site and does not allow fluid communication with either the second sealed space/negative-pressure zone or the ambient environment outside the negative-pressure dressing 605). In some embodiments, the gel layer 1305 may be adhesive and/or may function as an integral attachment device, such that a separate attachment device may not be necessary. In some embodiments, the gel layer 1305 may be sufficiently occlusive and/or non-porous to effectively seal the portion of the tissue site against negative pressure and/or to maintain the portion of the tissue site at ambient pressure, and no separate patch cover may be required. For example, such exemplary isolation patch 610 embodiments may consist essentially of the gel layer 1305 (or other force-dissipating pad) adhered to the portion of the tissue site (and/or may include the attachment device configured to attach the gel layer to the portion of the tissue site, in some embodiments).

In some embodiments, the isolation patch 610 may be configured to block negative pressure (e.g. shield the portion of the tissue site from negative pressure). For example, the seal provided by the isolation patch 610 may be sufficient to prevent migration of negative pressure from the surrounding negative-pressure dressing 605 into the isolation patch 610. In some embodiments, the isolation patch 610 may be configured to maintain or provide a pressure different than that of the negative-pressure dressing 605, for example approximately ambient atmospheric pressure, a positive pressure, or a negative pressure that is substantially less (e.g. closer to 0 mmHg) than that within the negative-pressure dressing.

Figure 14:
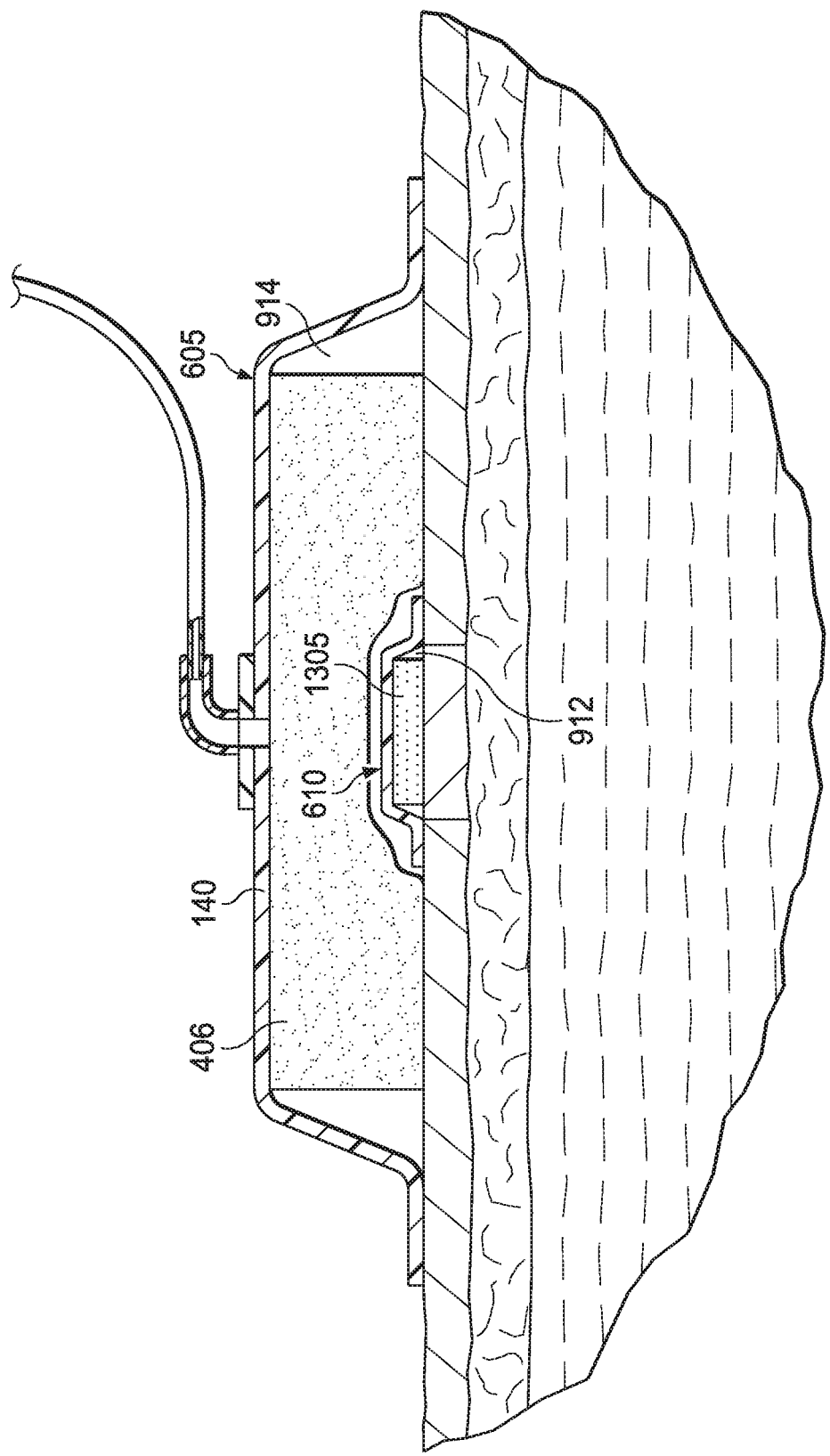
FIG. 14 is a schematic cross-section view of the dressing of FIG. 12 in place on an exemplary tissue site, illustrating additional details that may be associated with some embodiments.

FIG. 14 is a schematic cross-section view of the dressing 110 of FIG. 12 in place on an exemplary tissue site, illustrating additional details that may be associated with some embodiments. The dressing 110 embodiment of FIG. 14 may be similar to that of FIG. 9, except that the isolation patch 610 may be similar to that of FIG. 13 (e.g. unvented). Thus, in FIG. 14, there may be no vent or ventilation conduit, and the cover 140 of the negative-pressure dressing 605 may seal entirely around the perimeter of the negative-pressure dressing 605 (e.g. without any opening or anything passing out of the second sealed space 914 to the ambient environment). The isolation patch 610 may completely seal the portion of the tissue site (e.g. to prevent any fluid communication in or out of the first sealed space 912), and the negative-pressure dressing 605 may cover the isolation patch 610 and the tissue site (e.g. with the isolation patch 610 located within and surrounded by the second sealed space 914 of the negative-pressure dressing 605).

Methods, for providing negative pressure wound therapy to a tissue site, are also disclosed herein. For example, some method embodiments may comprise: fluidly isolating a portion of the tissue site from negative pressure; sealing the tissue site for negative-pressure wound therapy; and applying negative pressure to the tissue site, except at the isolated portion of the tissue site. In some embodiments, fluidly isolating a portion of the tissue site may comprise applying an isolation patch over/covering the portion of the tissue site; and sealing the tissue site may comprise applying a negative-pressure dressing over/covering the isolation patch and the tissue site. In some embodiments, applying an isolation patch may comprise sealing the isolation patch over the portion of the tissue site to form a first sealed space with ambient pressure; and applying a negative-pressure dressing may comprise sealing the negative-pressure dressing over the isolation patch and the tissue site, to form a second sealed space configured for negative-pressure therapy. Some embodiments may further comprise fluidly coupling the isolation patch to an ambient environment. For example, fluidly isolating a portion of the tissue site from negative pressure may further comprise fluidly coupling the first sealed space of the isolation patch to the ambient environment. Some embodiments may further comprise fluidly coupling the negative-pressure dressing to a negative-pressure source, so that negative pressure may be applied through the negative-pressure dressing to the tissue site, except for the portion of the tissue site isolated by the isolation patch.

In some embodiments, fluidly coupling the isolation patch to the ambient environment may comprise fluidly coupling a proximal end of a ventilation conduit to a patch manifold of the isolation patch through a patch cover for the isolation patch, and positioning a distal end of the ventilation conduit outside a cover for the negative-pressure dressing. In some embodiments, the ventilation conduit may not penetrate the cover for the negative-pressure dressing. For example, the ventilation conduit may pass between the cover for the negative-pressure dressing and the tissue site and/or may be sealed as it exits the negative-pressure dressing by an attachment device for the negative-pressure dressing (which may be located between the cover for the negative-pressure dressing and the tissue site). In some embodiments, fluidly coupling the isolation patch to the ambient environment may comprise fluidly coupling the isolation patch to a ventilation port in a cover for the negative-pressure dressing (e.g. so that the vent penetrates the cover for the negative-pressure dressing). In some embodiments, the isolation patch may comprise a gel layer, and fluidly isolating a portion of the tissue site from negative pressure may further comprise preventing substantially any fluid communication between the first sealed space and the second sealed space. In some embodiments, fluidly isolating the portion of the tissue site may also further comprise fluidly isolating the isolation patch (e.g. the first sealed space) from the ambient environment. For example, fluidly isolating the portion of the tissue site may comprise fluidly isolating the isolation patch (e.g. first sealed space) so that there is substantially no fluid communication in or out of the isolation patch. Some embodiments may further comprise resisting or reducing appositional and/or decompressive forces arising due to negative-pressure therapy. For example, the isolation patch may comprise a force-dissipating pad, such that applying the isolation patch may protect the portion of the tissue site from such forces. In some embodiments, the portion of the tissue site may comprise a nipple of a patient, and applying the isolation patch may comprise applying the isolation patch over the nipple. In some embodiments, the tissue site may comprise a breast of the patient, and applying the negative-pressure dressing may comprise applying the negative-pressure dressing over the breast. In some embodiments, the isolation patch may be applied to the portion of the tissue site before application of the negative-pressure dressing to the tissue site. In some embodiments, the isolation patch may be applied to the portion of the tissue site before application of negative pressure to the negative-pressure dressing. In some method embodiments, the dressing or dressing assembly may be similar to those two-part devices described herein.

The systems, apparatuses, and methods described herein may provide significant advantages. For example, in addition to the benefits of increased development of granulation tissue and reduced healing times, the system 100 can also reduce edema and bruising in a broader area of tissue surrounding or adjacent to a tissue site or treatment target, such as an incision. The dressing 110, for example, can reduce stress on an incision and maximize the treatment coverage area. The dressing 110 can also be beneficial for managing edema and bruising of tissue sites without an incision or open wound, such as a sprain. In some embodiments, the dressing may also allow more than one distinct pressure to be applied simultaneously to a tissue site, for example to different portions of the tissue site. For example, ambient pressure may be applied to a patient nipple (so that it does not undergo negative-pressure wound therapy), while the remainder of the breast tissue site may undergo negative-pressure wound therapy. Some embodiments of the dressing may exclude an area or portion of the tissue site from negative-pressure wound therapy, while providing negative-pressure wound therapy generally to the remainder of the tissue site. Some dressing embodiments may protect a portion of the tissue site from appositional and decompressive forces, for example when such forces arise during negative-pressure therapy.

If something is described as "exemplary" or an "example", it should be understood that refers to a non-exclusive example. The terms "about" or "approximately" or the like, when used with a number, may mean that specific number, or alternatively, a range in proximity to the specific number as understood by persons of skill in the art field (for example, +/−10%). Use of broader terms such as "comprises", "includes", and "having" should be understood to provide support for narrower terms such as "consisting of", "consisting essentially of", and "comprised substantially of". Use of the term "optionally", "may", "might", "possibly", "could", "can", "would", "should", "preferably", "typically", "often" and the like with respect to any element, component, feature, characteristic, etc. of an embodiment means that the element, component, feature, characteristic, etc. is not required, or alternatively, the element, component, feature, characteristic, etc. is required, both alternatives being within the scope of the embodiment(s). Such element, component, feature, characteristic, etc. may be optionally included in some embodiments, or it may be excluded (e.g. forming alternative embodiments, all of which are included within the scope of disclosure). Section headings used herein are provided for consistency and convenience, and shall not limit or characterize any invention(s) set out in any claims that may issue from this disclosure.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing, the container, or both may be eliminated or separated from other components for manufacture or sale. In other example configurations, the controller may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims. Also, features, elements, and aspects described with respect to a particular embodiment may be combined with features, elements, and aspects described with respect to one or more other embodiments.

What is claimed is:

1. A dressing assembly comprising:
a negative-pressure dressing configured for application of negative pressure to a tissue site; and
an isolation patch configured for use under the negative-pressure dressing and configured to isolate a portion of the tissue site from the negative pressure.

2. The dressing assembly of claim 1, wherein the isolation patch comprises a force-dissipating pad configured to resist appositional and/or decompressive forces.

3. The dressing assembly of claim 1, wherein the isolation patch is configured to prevent fluid communication between the isolation patch and the negative-pressure dressing.

4. The dressing assembly of claim 1, wherein:
the isolation patch comprises:
a first manifold;
a first cover configured to be disposed over the first manifold and to substantially prevent fluid flow therethrough;
a first attachment device configured to attach the first cover to the isolated portion of the tissue site and to form a seal preventing fluid communication between the isolated portion of the tissue site under the isolation patch and the remainder of the tissue site under the negative-pressure dressing; and
a vent configured to fluidly couple the first manifold to an ambient environment; and
the negative-pressure dressing comprises:
a second manifold;
a second cover configured to be disposed over the second manifold and to substantially prevent fluid flow therethrough; and
a second attachment device configured to attach the negative-pressure dressing to the tissue site and to form a seal preventing fluid communication between the tissue site and the ambient environment.

5. The dressing assembly of claim 1, wherein the isolation patch comprises a patch manifold, a patch cover configured to be disposed over the patch manifold, and a vent to ambient environment.

6. The dressing assembly of claim 5, wherein the isolation patch further comprises a patch attachment device configured to seal the patch cover to the portion of the tissue site.

7. The dressing assembly of claim 5, wherein the vent further comprises a ventilation conduit with a proximal end fluidly coupled to the patch manifold and a distal end configured to be located external to the negative-pressure dressing and fluidly coupled to the ambient environment.

8. The dressing assembly of claim 5, wherein the vent is configured to pass through the negative-pressure dressing.

9. The dressing assembly of claim 5, wherein the patch cover is occlusive with high MVTR.

10. The dressing assembly of claim 5, wherein the negative-pressure dressing comprises:
a dressing attachment device having a dressing treatment aperture;
a dressing manifold configured to be at least partially exposed to the tissue site through the dressing treatment aperture; and
a dressing cover configured to be disposed over the dressing manifold and coupled to the dressing attachment device around the dressing manifold.

11. The dressing assembly of claim 1, wherein the isolation patch comprises a gel layer and a patch cover configured to be disposed over the gel layer to form an outer surface of the isolation patch.

12. The dressing assembly of claim 11, wherein the negative-pressure dressing further comprises a dressing cover.

13. The dressing assembly of claim 1, wherein the isolation patch comprises a gel layer, and the gel layer is occlusive.

14. The dressing assembly of claim 11, wherein the isolation patch further comprises a patch attachment device configured to seal the patch cover of the isolation patch to the isolated portion of the tissue site.

15. The dressing assembly of claim 11, wherein the gel layer comprises TPE gel.

16. The dressing assembly of claim 11, wherein the negative-pressure dressing comprises:
a dressing attachment device having a dressing treatment aperture;
a dressing manifold configured to be at least partially exposed to the tissue site through the dressing treatment aperture; and
a dressing cover configured to be disposed over the dressing manifold and coupled to the dressing attachment device around the dressing manifold.

17. A system comprising:
a negative-pressure dressing configured for application of negative pressure to a tissue site;
an isolation patch, configured for use under the negative-pressure dressing and configured to fluidly isolate a portion of the tissue site from the negative pressure; and
a negative-pressure source fluidly coupled to the negative-pressure dressing.

18. A method for using a dressing assembly on a tissue site, further comprising:
applying an isolation patch to a portion of the tissue site; and
applying a negative-pressure dressing to the tissue site, over the isolation patch; wherein:
applying the isolation patch comprises sealing the isolation patch over the portion of the tissue site to form a first sealed space with ambient pressure; and
applying the negative-pressure dressing comprises sealing the negative-pressure dressing over the isolation patch and the tissue site, to form a second sealed space configured for negative pressure wound therapy.

19. The method of claim 18, further comprising fluidly coupling the isolation patch to an ambient environment.

20. The method of claim 18, further comprising fluidly coupling the negative-pressure dressing to a negative-pressure source and applying negative pressure through the negative-pressure dressing to the tissue site, except for the portion of the tissue site isolated by the isolation patch.

21. The dressing assembly of claim 1, wherein the isolation patch is configured to cover a nipple of a patient, and the negative-pressure dressing is configured to cover a breast of the patient.

22. The dressing assembly of claim 5, wherein the isolation patch further comprises a patch tissue contact layer coupled to the patch manifold and configured to allow fluid communication from the tissue site to the patch manifold.

23. A dressing for use on a tissue site, comprising a negative-pressure zone; and a zone of ambient pressure fluidly isolated from the negative-pressure zone by an isolation patch configured to be disposed within or underneath the dressing.

24. The dressing of claim 23, wherein the negative-pressure zone and the zone of ambient pressure have no fluid communication therebetween.

25. The dressing of claim 23, wherein the negative-pressure zone is formed by the negative-pressure dressing configured for negative-pressure therapy at the tissue site; and the zone of ambient pressure is formed by the isolation patch configured to underlie the negative-pressure dressing and to maintain ambient environment pressure at a portion of the tissue site.

26. The dressing of claim 23, wherein the negative-pressure zone is configured to surround the zone of ambient pressure over the tissue site.

27. A method for providing negative pressure wound therapy to a tissue site, comprising:
  fluidly isolating a portion of the tissue site from negative pressure using an isolation patch configured for use under a negative-pressure dressing;
  sealing the tissue site for negative-pressure wound therapy around or over the isolation patch; and
  applying negative pressure to the tissue site, except at the isolated portion of the tissue site.

* * * * *